(12) United States Patent
Brown et al.

(10) Patent No.: US 10,308,628 B2
(45) Date of Patent: Jun. 4, 2019

(54) HETEROCYCLIC COMPOUNDS AND METHODS FOR THEIR USE

(71) Applicant: NOVARTIS AG, Basel (CH)

(72) Inventors: Jane Brown, Bingham (GB); Thomas David McCarthy, Westport, CT (US); Alan Naylor, Royston (GB); John Paul Watts, Southwell (GB)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/556,593

(22) PCT Filed: Mar. 9, 2016

(86) PCT No.: PCT/IB2016/051318
§ 371 (c)(1),
(2) Date: Sep. 7, 2017

(87) PCT Pub. No.: WO2016/142867
PCT Pub. Date: Sep. 15, 2016

(65) Prior Publication Data
US 2018/0057477 A1  Mar. 1, 2018

(30) Foreign Application Priority Data

Mar. 12, 2015 (AU) .................................. 201500878
Jul. 15, 2015 (AU) ................................. 2015902830

(51) Int. Cl.
*C07D 401/04* (2006.01)
*C07D 413/04* (2006.01)

(52) U.S. Cl.
CPC ......... *C07D 401/04* (2013.01); *C07D 413/04* (2013.01)

(58) Field of Classification Search
CPC ........................... C07D 401/04; C07D 413/04
See application file for complete search history.

(56) References Cited

U.S. PATENT DOCUMENTS 7,795,275 B2    9/2010  Smith et al.
2017/0369473 A1  12/2017  Brown et al.

FOREIGN PATENT DOCUMENTS

| WO | 2003/037890 A1 | 5/2003 |
| WO | 2006/066361 A1 | 6/2006 |
| WO | 2013/102242 A1 | 7/2013 |
| WO | 2013/110135 A1 | 8/2013 |
| WO | 2016/113668 A1 | 7/2016 |

*Primary Examiner* — Bruck Kifle
(74) *Attorney, Agent, or Firm* — Wendy F. Ballard, J.D.

(57) ABSTRACT

The present invention relates to heterocyclic compounds useful for antagonising angiotensin II Type 2 ($AT_2$) receptor. More particularly the invention relates to compounds of formula (I), as described herein, compositions containing them and their use in methods of treating or preventing disorders or diseases associated with $AT_2$ receptor function including neuropathic pain, inflammatory pain, conditions associated with neuronal hypersensitivity, impaired nerve conduction velocity, cell proliferation disorders, disorders associated with an imbalance between bone resorption and bone formation and disorders associated with aberrant nerve regeneration.

15 Claims, No Drawings

HETEROCYCLIC COMPOUNDS AND METHODS FOR THEIR USE

This application is a U.S. national Phase filing of International Serial No. PCT/IB2016/051318 filed Mar. 9, 2016, and claims priority to Australian application Serial No. 2015902830 filed Mar. 12, 2015 and Australian application Serial No. 2015902830 filed Jul. 17, 2015, the contents of which are incorporated herein by reference in their entirety.

FIELDS OF THE INVENTION

The present invention relates generally to compounds that are useful in antagonizing the angiotensin II type 2 ($AT_2$) receptor. More particularly, the invention relates to heterocyclic compounds of formula (I) and their use as $AT_2$ receptor antagonists. Pharmaceutical compositions comprising the compounds and their use in modulating the $AT_2$ receptor and therapies that require modulation of the $AT_2$ receptor are described.

BACKGROUND OF THE INVENTION

Although the $AT_2$ receptor has been known since the 1980s, much less is known about its biological function than the angiotensin II type 1 ($AT_1$) receptor, which has been studied for its functional effects on vasoconstriction, aldosterone release and cardiovascular growth [Wexler et al., 1996]. However, more recently the $AT_2$ receptor has been implicated in the differentiation and regeneration of neuronal tissue [Steckelings et al., 2005; Chakrabarty et al., 2008], cell proliferation and angiogenesis [Clere et al., 2010] and maintenance of bone mass [Izu et al., 2009].

$AT_2$ receptor antagonists have also recently been associated with the treatment of pain, particularly inflammatory pain [WO 2007/106938] and neuropathic pain [WO 2006/066361], two types of pain which are difficult to treat or relieve. Impaired nerve conduction velocity is also associated with nerve damage and has been implicated in peripheral neuropathies, Carpel Tunnel Syndrome, ulnar neuropathy, Guillian-Barré Syndrome, fascioscapulohumeral muscular dystrophy and spinal disc herneation. Impaired nerve conduction velocity can result in diminished reflex responses and altered peripheral sensation such as parathesia and in some cases pain and $AT_2$ receptor antagonists have been shown to restore nerve conduction velocity [WO 2011/088504].

While there are effective therapies for treating nociceptive pain, inflammatory and neuropathic pain are often resistant to these therapies. In addition, current therapies of neuropathic pain, inflammatory pain, impaired nerve conduction velocity and other types of pain that are difficult to treat, have serious side effects, for example, cognitive changes, sedation, nausea and in the case of narcotic drugs, tolerance and dependence. There is a need for further therapies that treat or prevent neuropathic pain, inflammatory pain, impaired nerve conduction velocity and other painful conditions that are currently difficult to treat.

Cell proliferation and angiogenesis are important biological functions in normal tissue. However, uncontrolled cell proliferation and angiogenesis can lead to tumors and other proliferative disorders. While there are some effective chemotherapies available for tumors, many result in unpleasant side effects and/or have high toxicity for normal cells. Further therapies for reducing or preventing abnormal cell proliferation in a controlled manner are required and $AT_2$ receptor antagonists have been shown to have antiproliferative activity [Clere et al., 2010].

Osteoporosis is a significant problem in older populations, especially in post-menopausal women. Current therapies for osteoporosis rely on calcium supplementation. However, the control of bone formation and bone resorption is complex and further therapies for improving bone mass are required and $AT_2$ receptor antagonists have been shown to increase bone mass [Izu et al., 2009].

The role of the $AT_2$ receptor in modulating neuronal outgrowth and associated effects of $AT_2$ receptor antagonists on reducing neuronal outgrowth, indicates that $AT_2$ receptor antagonists may be useful therapeutics in diseases characterized by aberrant nerve regeneration [Chakrabarty et al., 2008].

Heterocyclic $AT_2$ receptor antagonists are known to have activity in treatment of neuropathic pain, inflammatory pain, impaired nerve conduction velocity, cell proliferative disorders, conditions associated with conditions characterized by neuronal hypersensitivity, disorders associated with an imbalance between bone resorption and bone formation and disorders associated with aberrant nerve regeneration (WO 2013/102242, WO 2013/110134 and WO 2013/110135).

However, the present invention is predicated in part on the discovery of new heterocyclic compounds that have improved $AT_2$ receptor antagonist activity.

SUMMARY OF THE INVENTION

In a first aspect of the present invention there is provided a compound of formula (I):

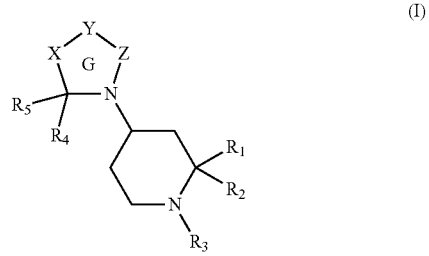

wherein Ring G is a 5 to 8 membered ring and

X is absent or is selected from —$(CR_6R_7)_n$—, —W—, —$(CR_6R_7)_m$—W—, —W—$(CR_6R_7)_m$— and —$(CR_6R_7)_p$—W—$(CR_6R_7)_p$—;

Y is —$CR_8CR_9$— wherein $R_8$ and $R_9$ together with the carbon atoms to which they are attached form an optionally substituted aromatic or heteroaromatic ring or ring system;

Z is absent or is selected from —$CR_4R_5$—, —$CR_6R_7CR_4R_5$— and —W—$(CR_4R_5)$—;

W is selected from —O—, —S—, —S(O)—, —$S(O)_2$—, —C(O)—, —$NR_{10}$—, —$C(O)N(R_{11})$—, —$N(R_{11})C(O)$—, —C(O)O—, —OC(O)—, —$S(O)_2N(R_{11})$—, —$N(R_{11})S(O)_2$—, —$N(R_{11})C(O)N(R_{11})$— and —$N(R_{11})S(O)_2N(R_{11})$—;

$R_1$ is selected from —$CO_2H$, —$CH_2CO_2H$, —C(O)C(O)OH, —$CH_2OH$, —$C(O)NH_2$, —CN, —$CH_2C(O)NH_2$, —$CH_2CN$, a carboxylic acid bioisostere and —$CH_2$carboxylic acid bioisostere;

$R_2$ is selected from hydrogen, alkyl, alkenyl, alkynyl, —$C_{1-6}$alkylene$R_{12}$, —$C_{2-6}$alkenylene$R_{12}$ and —$C_{2-6}$alkylene$R_{12}$;

$R_3$ is selected from —C(O)CH(aryl)(aryl) and —C(O)N(aryl)(aryl);

Each $R_4$ and $R_5$ are independently selected from hydrogen, alkyl, alkenyl, alkynyl, —OC($R_{14}$)$_3$, —CN, —NO$_2$, —N($R_{13}$)$_2$, —CO$_2R_{13}$, —C(O)$R_{13}$, —C(O)N($R_{13}$)$_2$, —S(O)$_2$ $R_{13}$, —S(O)$_2$N($R_{13}$)$_2$, —C($R_{14}$)$_3$, cycloalkyl, cycloalkenyl, aryl, heterocyclyl and heteroaryl, or $R_4$ and $R_5$ taken together from a carbonyl group;

$R_6$ and $R_7$ are independently selected from hydrogen, alkyl, alkenyl, alkynyl, —O$R_{13}$, —S$R_{13}$, halo, —CN, —NO$_2$, —N($R_{13}$)$_2$, —CO$_2R_{13}$, —C(O)$R_{13}$, —C(O)N($R_{13}$)$_2$, —S(O)$_2R_{13}$, S(O)$_2$N($R_{13}$)$_2$, —C($R_{14}$)$_3$, —OC($R_{14}$)$_3$, cycloalkyl, cycloalkenyl, aryl, heterocyclyl and heteroaryl, or $R_6$ and $R_7$ taken together form a carbonyl group;

$R_{10}$ is selected from hydrogen, alkyl, alkenyl, alkynyl, cycloalkyl, cycloalkenyl, aryl, heterocyclyl, heteroaryl, —C($R_{14}$)$_3$, —C(O)$R_{13}$, —C(O)N($R_{13}$)$_2$, —S(O)$R_{13}$, —S(O)$_2R_{13}$, —S(O)$_2$N($R_{13}$)$_2$ and —CO$_2R_{13}$;

$R_{11}$ is selected from hydrogen and alkyl;

$R_{12}$ is selected from cycloalkyl, cycloalkenyl, aryl, heterocyclyl and heteroaryl;

Each $R_{13}$ is independently selected from hydrogen, alkyl, alkenyl, alkynyl, cycloalkyl, cycloalkenyl, aryl, heterocyclyl and heteroaryl;

Each $R_{14}$ is independently selected from hydrogen and halo;

n is selected from an integer from 1 to 4;

m is selected from an integer from 1 to 3;

p is selected from an integer of 1 or 2;

wherein each alkyl, alkenyl, alkynyl, cycloalkyl, cycloalkenyl, aryl, heterocyclyl and heteroaryl may be optionally substituted; or a pharmaceutically acceptable salt thereof.

In another aspect, the present invention provides a pharmaceutical composition comprising the compounds of formula (I) or a pharmaceutically acceptable salt thereof and a pharmaceutically acceptable carrier.

In a further aspect of the invention there is provided a method of treating or preventing neuropathic pain in a subject comprising administering a compound of formula (I) or a pharmaceutically acceptable salt thereof.

In yet a further aspect of the invention there is provided a method of treating or preventing a condition characterized by neuronal hypersensitivity in a subject comprising administering a compound of formula (I) or a pharmaceutically acceptable salt thereof.

In yet another aspect of the invention there is provided a method of treating or preventing inflammatory pain in a subject comprising administering a compound of formula (I) or a pharmaceutically acceptable salt thereof.

In a further aspect, the present invention provides a method of treating or preventing impaired nerve conduction velocity in a subject comprising administering a compound of formula (I) or a pharmaceutically acceptable salt thereof.

In yet a further aspect of the invention there is provided a method of producing analgesia in a subject comprising administering a compound of formula (I) or a pharmaceutically acceptable salt thereof.

In still another aspect of the invention there is provided a method of treating or preventing a cell proliferative disorder in a subject comprising administering a compound of formula (I) or a pharmaceutically acceptable salt thereof.

In a further aspect the present invention provides a method of treating or preventing a disorder associated with an imbalance between bone resorption and bone formation in a subject comprising administering a compound of formula (I) or a pharmaceutically acceptable salt thereof.

In yet another aspect the present invention provides a method of treating a disorder associated with aberrant nerve regeneration in a subject comprising administering a compound of formula (I) or a pharmaceutically acceptable salt thereof.

DESCRIPTION OF THE INVENTION

Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

As used herein, the term "about" refers to a quantity, level, value, dimension, size, or amount that varies by as much as 30%, 25%, 20%, 15% or 10% to a reference quantity, level, value, dimension, size, or amount.

As used herein, the term "AT$_2$ receptor" means an angiotensin II type 2 (AT$_2$) receptor polypeptide that can bind angiotensin II and/or one or more other ligands. The term "AT$_2$ receptor" encompasses vertebrate homologs of AT$_2$ receptor family members, including, but not limited to, mammalian, reptilian and avian homologs. Representative mammalian homologs of AT$_2$ receptor family members include, but are not limited to, murine and human homologs.

The term "antagonist" as used herein refers to a compound that decreases or inhibits the biological activity and/or function of an AT$_2$ receptor, including binding to the AT$_2$ receptor and blocking access to angiotensin II, inhibiting a gene that expresses AT$_2$ receptor, or inhibiting an expression product of that gene. By the term "selective", is meant that the compound binds to and/or inhibits AT$_2$ receptor activity to a greater extent than binding and inhibition of the AT$_1$ receptor. In some instances, selective refers to binding and/or inhibition of the AT$_2$ receptor with little or no binding at the AT$_1$ receptor.

The term "allodynia" as used herein refers to the pain that results from a non-noxious stimulus i.e. pain due to a stimulus that does not normally provoke pain. Examples of allodynia include, but are not limited to, cold allodynia, tactile allodynia (pain due to light pressure or touch), and the like.

The term "analgesia" is used herein to describe states of reduced pain perception, including absence from pain sensations as well as states of reduced or absent sensitivity to noxious stimuli. Such states of reduced or absent pain perception are induced by the administration of a pain-controlling agent or agents and occur without loss of consciousness, as is commonly understood in the art. The term analgesia encompasses the term "antinociception", which is used in the art as a quantitative measure of analgesia or reduced pain sensitivity in animal models.

The term "anti-allodynia" is used herein to describe states of reduced pain perception, including absence from pain sensations as well as states of reduced or absent sensitivity to non-noxious stimuli. Such states of reduced or absent pain perception are induced by the administration of a pain-controlling agent or agents and occur without loss of consciousness, as is commonly understood in the art.

The term "causalgia" as used herein refers to the burning pain, allodynia, and hyperpathia after a traumatic nerve lesion, often combined with vasomotor and sudomotor dysfunction and later trophic changes.

By "complex regional pain syndromes" is meant the pain that includes, but is not limited to, reflex sympathetic dystrophy, causalgia, sympathetically maintained pain, and the like.

By "condition characterized by neuronal hypersensitivity" is meant conditions that have symptoms of pain related to neuronal hypersensitivity and/or allodynia. Examples of this type of condition include fibromyalgia and irritable bowel syndrome.

By "disorder associated with aberrant nerve regeneration" is meant disorders in which there is abnormal axon outgrowth in neurons. This abnormal outgrowth may be associated with painful conditions including breast pain, interstitial cystitis, vulvodynia and cancer chemotherapy-induced neuropathies.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "hyperalgesia" is meant an increased response to a stimulus that is normally considered painful. A hyperalgesia condition is one that is associated with increased pain caused by a stimulus that is normally mildly or minimally painful.

By "neuropathic pain" is meant any pain syndrome initiated or caused by a primary lesion or dysfunction in the peripheral or central nervous system. Examples of neuropathic pain include, but are not limited to, thermal or mechanical hyperalgesia, thermal or mechanical allodynia, diabetic pain, entrapment pain, and the like.

The term "nociceptive pain" refers to the normal, acute pain sensation evoked by activation of nociceptors located in non-damaged skin, viscera and other organs in the absence of sensitization.

As used herein "inflammatory pain" refers to pain induced by inflammation. Such types of pain may be acute or chronic and can be due to any number of conditions characterized by inflammation including, without limitation, burns including chemical, frictional or thermal burns, autoimmune diseases such as rheumatoid arthritis, osteoarthritis and inflammatory bowel disease including Crohn's disease and colitis, as well as other inflammatory diseases including carditis, dermatitis, myositis, neuritis and collagen vascular diseases.

The term "pain" as used herein is given its broadest sense and includes an unpleasant sensory and emotional experience associated with actual or potential tissue damage, or described in terms of such damage and includes the more or less localized sensation of discomfort, distress, or agony, resulting from the stimulation of specialized nerve endings. There are many types of pain, including, but not limited to, lightning pains, phantom pains, shooting pains, acute pain, inflammatory pain, neuropathic pain, complex regional pain, neuralgia, neuropathy, and the like (Dorland's Illustrated Medical Dictionary, 28$^{th}$ Edition, W. B. Saunders Company, Philadelphia, Pa.). The goal of treatment of pain is to reduce the degree of severity of pain perceived by a treatment subject.

By the phrases "impaired NCV" or "impaired nerve conduction velocity" and the like is meant any nerve conduction demonstrably abnormal in any one of the parameters assessed for normal nerve signal conduction. Whether the various parameters of NCV are normal is typically an assessment made by the relevant trained clinician. General background, terminology and procedures known to those in the art for evaluating NCV are described in "Proper performance and interpretation of electrodiagnostic studies' Muscle Nerve. (2006) 33(3):436-439 and "Electrodiagnostic medicine listing of sensory, motor, and mixed nerves." Appendix J of Current Procedural Terminology (CPT) 2007, authored by The American Association of Neuromuscular & Electrodiagnostic Medicine and published by the American Medical Association. Impaired or abnormal nerve conduction velocity is a symptom of nerve dysfunction or damage and may be causal to or a symptom of a large number of diseases or disorders, particularly diseases or disorders that exhibit diminished reflex responses and altered peripheral sensation including paresthesia. As used herein, "paresthesia" refers to a sensation of tingling, prickling, weakness or numbness in a subject's skin. It is also known as "pins and needles" or a limb "falling asleep". Paresthesia may be transient, acute or chronic and may occur alone or be accompanied by other symptoms such as pain.

As used herein, the term "cell proliferative disorder" refers to diseases or conditions where unwanted or damaged cells are not removed by normal cellular process, or diseases or conditions in which cells undergo aberrant, unwanted or inappropriate proliferation. Disorders characterized by inappropriate cell proliferation include, for example, inflammatory conditions such as inflammation arising from acute tissue injury including, for example, acute lung injury, cancer including cancers characterized by tumors, autoimmune disorders, tissue hypertrophy and the like.

The term "disorder associated with an imbalance between bone resorption and bone formation" includes disorders where there is insufficient development of bone mass, excessive bone resorption and insufficient bone formation during remodelling. An exemplary disorder associated with an imbalance between bone resorption and bone formation is osteoporosis.

As used herein, the term "alkyl" refers to a straight chain or branched saturated hydrocarbon group having 1 to 10 carbon atoms. Where appropriate, the alkyl group may have a specified number of carbon atoms, for example, $C_{1-6}$alkyl which includes alkyl groups having 1, 2, 3, 4, 5 or 6 carbon atoms in a linear or branched arrangement. Examples of suitable alkyl groups include, but are not limited to, methyl, ethyl, n-propyl, i-propyl, n-butyl, i-butyl, t-butyl, n-pentyl, 2-methylbutyl, 3-methylbutyl, n-hexyl, 2-methylpentyl, 3-methylpentyl, 4-methylpentyl, 2-ethylbutyl, 3-ethylbutyl, heptyl, octyl, nonyl and decyl.

As used herein, the term "alkenyl" refers to a straight-chain or branched hydrocarbon group having one or more double bonds between carbon atoms and having 2 to 10 carbon atoms. Where appropriate, the alkenyl group may have a specified number of carbon atoms. For example, $C_2$-$C_6$ as in "$C_2$-$C_6$alkenyl" includes groups having 2, 3, 4, 5 or 6 carbon atoms in a linear or branched arrangement. Examples of suitable alkenyl groups include, but are not limited to, ethenyl, propenyl, isopropenyl, butenyl, butadienyl, pentenyl, pentadienyl, hexenyl, hexadienyl, heptenyl, octenyl, nonenyl and decenyl.

As used herein, the term "alkynyl" refers to a straight-chain or branched hydrocarbon group having one or more triple bonds and having 2 to 10 carbon atoms. Where appropriate, the alkynyl group may have a specified number of carbon atoms. For example, $C_2$-$C_6$ as in "$C_2$-$C_6$alkynyl" includes groups having 2, 3, 4, 5 or 6 carbon atoms in a linear or branched arrangement. Examples of suitable alkynyl groups include, but are not limited to ethynyl, propynyl, butynyl, pentynyl and hexynyl.

As used herein, the term "alkylene" refers to a divalent saturated hydrocarbon chain having 1 to 6 carbon atoms. Where appropriate, the alkylene group may have a specified number of carbon atoms, for example, $C_{1-6}$alkylene includes alkylene groups having 1, 2, 3, 4, 5 or 6 carbon atoms in a linear arrangement. Examples of suitable alkylene groups include, but are not limited to, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$—.

As used herein, the term "alkenylene" refers to a divalent unsaturated hydrocarbon chain having 2 to 6 carbon atoms and at least one double bond. Where appropriate, the alkenylene group may have a specified number of carbon atoms, for example, $C_{2-6}$alkenylene includes alkenylene groups having 2, 3, 4, 5 or 6 carbon atoms in a linear arrangement. The double bonds may be in either E or Z configuration. Examples of suitable alkenylene groups include, but are not limited to, —CH=CH—, —CH=CHCH$_2$—, —CH$_2$CH=CH—, —CH=CHCH$_2$CH$_2$—, —CH$_2$CH=CHCH$_2$—, —CH$_2$CH$_2$CH=CH—, —CH=CHCH$_2$CH$_2$CH$_2$—, —CH$_2$CH=CHCH$_2$CH$_2$—, —CH$_2$CH$_2$CH=CHCH$_2$—, —CH$_2$CH$_2$CH$_2$CH=CH—, —CH=CHCH$_2$CH$_2$CH$_2$CH$_2$— —CH$_2$CH=CHCH$_2$CH$_2$CH$_2$—, —CH$_2$CH$_2$CH=CHCH$_2$CH$_2$—, —CH$_2$CH$_2$CH$_2$CH=CHCH$_2$— and —CH$_2$CH$_2$CH$_2$CH$_2$CH=CH—.

As used herein, the term "alkynylene" refers to a divalent unsaturated hydrocarbon chain having 2 to 6 carbon atoms and at least one triple bond. Where appropriate, the alkynylene group may have a specified number of carbon atoms, for example, $C_{2-6}$alkynylene includes alkynylene groups having 2, 3, 4, 5 or 6 carbon atoms in a linear arrangement. Examples of suitable alkynylene groups include, but are not limited to, —C≡C—, —C≡CCH$_2$—, —CH$_2$C≡C—, —C≡CCH$_2$CH$_2$—, —CH$_2$C≡CCH$_2$—, —CH$_2$CH$_2$C≡C—, —C≡CCH$_2$CH$_2$CH$_2$—, —CH$_2$C≡CCH$_2$CH$_2$—, —CH$_2$CH$_2$C≡CCH$_2$—, —CH$_2$CH$_2$CH$_2$C≡C—, —C≡CCH$_2$CH$_2$CH$_2$CH$_2$—, —CH$_2$C≡CCH$_2$CH$_2$CH$_2$—, —CH$_2$CH$_2$C≡CCH$_2$CH$_2$—, —CH$_2$CH$_2$CH$_2$C≡CCH$_2$— and —CH$_2$CH$_2$CH$_2$CH$_2$C≡C—.

In some embodiments, one or more "—CH$_2$—" groups in an alkylene, alkenylene or alkynylene group may be replaced by a heteroatom or a group containing a heteroatom including —O—, —S—, —NR—, —S(O)—, —S(O)$_2$—, —C(O)—, —C(O)NR— and —NHC(O)—, where R is hydrogen or alkyl.

As used herein, the term "cycloalkyl" refers to a saturated cyclic hydrocarbon. The cycloalkyl ring may include a specified number of carbon atoms. For example, a 3 to 8 membered cycloalkyl group includes 3, 4, 5, 6, 7 or 8 carbon atoms. Examples of suitable cycloalkyl groups include, but are not limited to, cyclopropyl, cyclobutyl, cyclopentyl, cyclohexyl, cycloheptyl and cyclooctyl.

As used herein, the term "cycloalkenyl" refers to an unsaturated cyclic hydrocarbon. The cycloalkenyl ring may include a specified number of carbon atoms. For example, a 5 to 8 membered cycloalkenyl group includes 5, 6, 7 or 8 carbon atoms. The cycloalkenyl group has one or more double bonds and when more than one double bond is present, the double bonds may be unconjugated or conjugated, however the cycloalkenyl group is not aromatic. Examples of suitable cycloalkenyl groups include, but are not limited to, cyclopentenyl, cyclopentadienyl, cyclohexenyl, cyclohexadienyl, cycloheptenyl, cycloheptadienyl, cycloheptatrienyl, cyclooctenyl, cyclooctadienyl and cyclooctatrienyl rings.

As used herein, the term "aryl" is intended to mean any stable, monocyclic, bicyclic or tricyclic carbon ring system of up to 7 atoms in each ring, wherein at least one ring is aromatic. Examples of such aryl groups include, but are not limited to, phenyl, naphthyl, tetrahydronaphthyl, indanyl, indenyl, fluorenyl, phenanthrenyl, biphenyl and binaphthyl.

The term "benzyl" where used herein refers to a phenylmethylene group, $C_6H_5CH_2$—.

As used herein, the term "halogen" or "halo" refers to fluorine (fluoro), chlorine (chloro), bromine (bromo) and iodine (iodo).

The term "heterocyclic" or "heterocyclyl" as used herein, refers to a cyclic hydrocarbon in which one to four carbon atoms have been replaced by heteroatoms independently selected from the group consisting of N, N(R), S, S(O), S(O)$_2$ and O. A heterocyclic ring may be saturated or unsaturated but not aromatic. A heterocyclic group may also be part of a spirocyclic group containing 1, 2 or 3 rings, two of which are in a "spiro" arrangement. Examples of suitable heterocyclyl groups include azetidine, tetrahydrofuranyl, tetrahydrothiophenyl, pyrrolidinyl, 2-oxopyrrolidinyl, pyrrolinyl, pyranyl, dioxolanyl, piperidinyl, 2-oxopiperidinyl, pyrazolinyl, imidazolinyl, thiazolinyl, dithiolyl, oxathiolyl, dioxanyl, dioxinyl, dioxazolyl, oxathiozolyl, oxazolonyl, piperazinyl, morpholino, thiomorpholinyl, 3-oxomorpholinyl, dithianyl, trithianyl and oxazinyl.

The term "heteroaryl" as used herein, represents a stable monocyclic, bicyclic or tricyclic ring of up to 8 atoms in each ring, wherein at least one ring is aromatic and at least one ring contains from 1 to 4 heteroatoms selected from the group consisting of O, N and S. Heteroaryl groups within the scope of this definition include, but are not limited to, acridinyl, carbazolyl, cinnolinyl, coumarinyl, quinoxalinyl, quinazolinyl, pyrazolyl, indolyl, isoindolyl, indolinyl, indazolyl, benzimidazolyl, 1H,3H-1-oxoisoindolyl, benzotriazolyl, furanyl, thienyl, thiophenyl, benzothienyl, benzofuranyl, benzodioxolanyl, benzodioxanyl, benzodioxinyl, quinolinyl, isoquinolinyl, oxazolyl, isoxazolyl, benzoxazolyl, benzothiazolyl, benzopyranyl, imidazolyl, pyrazinyl, pyridazinyl, pyridinyl, pyrimidinyl, pyrrolyl, tetrahydroquinolinyl, thiazolyl, isothiazolyl, 1,2,3-triazolyl, 1,2,4-triazolyl, 1,2,4-oxadiazolyl, 1,2,4-thiadiazolyl, 1,3,5-triazinyl, 1,2,4-triazinyl, 1,2,4,5-tetrazinyl, tetrazolyl, cyclopentyl[b]pyridinyl, benzodithiolyl, benzodihydrodithiolyl, benzodithanyl, naphthyridinyl, phthalazinyl, benzoxazinyl, benzoxadiazinyl and pteridinyl. Particular heteroaryl groups have 5- or 6-membered rings, such as pyrazolyl, furanyl, thienyl, oxazolyl, indolyl, isoindolyl, 1H,3H-1-oxoisoindolyl, isoxazolyl, imidazolyl, pyrazinyl, pyridazinyl, pyridinyl, pyrimidinyl, pyrrolyl, thiazolyl, isothiazolyl, 1,2,3-triazolyl, 1,2,4-triazolyl and 1,2,4-oxadiazolyl and 1,2,4-thiadiazolyl.

Each alkyl, alkenyl, alkynyl, cycloalkyl, cycloalkenyl, aryl, heterocyclyl and heteroaryl whether an individual entity or as part of a larger entity may be optionally substituted with one or more optional substituents selected from the group consisting of $C_{1-6}$alkyl, $C_{2-6}$alkenyl, $C_{3-6}$cycloalkyl, cycloalkenyl, oxo (=O), —OH, —SH, $C_{1-6}$alkylO—, $C_{2-6}$alkenylO—, $C_{3-6}$cycloalkylO—, —Ocycloalkenyl, $C_{1-6}$alkylS—, $C_{2-6}$alkenylS—, $C_{3-6}$cycloalkylS—, cycloalkenylS—, —CO$_2$H, —CO$_2C_{1-6}$alkyl, —NH$_2$, —NH($C_{1-6}$alkyl), —N($C_{1-6}$alkyl)$_2$, —NH(phenyl), —N(phenyl)$_2$, —CN, —NO$_2$, -halogen, —CF$_3$, —OCF$_3$, —SCF$_3$, —CHF$_2$, —OCHF$_2$, —SCHF$_2$, —CH$_2$F, —OCH$_2$F, —SCH$_2$F, -phenyl, -heterocyclyl, -heteroaryl, -Oheteroaryl, -Oheterocyclyl, —Ophenyl, —C(=O)$_p$henyl, —C(=O)C$_{1-6}$alkyl, —SO$_2$H, —SO$_2$C$_{1-6}$alkyl, —SO$_2$phenyl, —SO$_2$NH$_2$, —SO$_2$NH(C$_{1-6}$alkyl), —SO$_2$N(C$_{1-6}$alkyl)$_2$, —SO$_2$NH(phenyl), —SO$_2$N(phenyl)$_2$, —CONH$_2$, —CONH(C$_{1-6}$alkyl), —CON(C$_{1-6}$alkyl)$_2$, —CONH(phenyl) and —CON(phenyl)$_2$. Examples of suitable substituents include, but are not limited to, methyl, ethyl, propyl, isopropyl, butyl, sec-butyl, tert-butyl, vinyl, methoxy, ethoxy, propoxy, isopropoxy, butoxy, methylthio, ethylthio, propylthio, isopropylthio, butylthio, hydroxy, hydroxymethyl, hydroxyethyl, hydroxypropyl, hydroxybutyl, oxo, fluoro, chloro, bromo, iodo, cyano, nitro, —CO$_2$H, —CO$_2$CH$_3$, —CONH$_2$, —SO$_2$CH$_3$, —SO$_2$phenyl, —CONH(CH$_3$), —CON(CH$_3$)$_2$, —SO$_2$NH$_2$, —SO$_2$NH(CH$_3$), —SO$_2$N(CH$_3$)$_2$, trifluoromethyl, trifluoromethoxy, trifluoromethylthio, difluoromethyl, difluoromethoxy, difluoromethylthio, fluoromethyl, fluoromethoxy, fluoromethylthio, morpholino, amino, methylamino, dimethylamino, phenyl, phenoxy, phenylcarbonyl, benzyl and acetyl.

The term "carboxylic acid bioisotere" refers to a group which is physiochemically or topologically similar to carboxylic acid or carboxylate group. Examples of suitable carboxylic acid or carboxylate isosteres include, but are not limited to, tetrazole, tetrazolate, —CONH-tetrazole, oxadiazole, phosphate (—PO$_3$H$_2$), —C(OH)(CF$_3$)$_2$, N-(aryl or heteroaryl)-sulfonamides, acylsulfonamides and sulfonic acid (—SO$_3$H) [See Patani and LaVoie, 1996]. Examples of sulfonamide isosteric equivalents of carboxy groups include —C(=O)NHSO$_2$R$^a$, —C(=O)NHSO$_2$N(R$^a$)$_2$, —C(=O)NHSO$_2$NH(R$^a$), —SO$_2$NHC(=O)R$^a$, —SO$_2$NHC(=O)NHR$^a$, —SO$_2$NHR$^a$ and —NHSO$_2$R$^a$, where R$^a$ is selected from the group consisting of C$_{1-6}$alkyl, C$_{2-6}$alkenyl, C$_{3-8}$cycloalkyl, aryl, heterocyclyl, heteroaryl and —CF$_3$.

The compounds of the invention may be in the form of pharmaceutically acceptable salts. It will be appreciated however that non-pharmaceutically acceptable salts also fall within the scope of the invention since these may be useful as intermediates in the preparation of pharmaceutically acceptable salts or may be useful during storage or transport. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, toluenesulphonic, benezenesulphonic, salicylic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, ammonium and alkylammonium.

Basic nitrogen-containing groups may be quaternized with such agents as lower alkyl halide, such as methyl, ethyl, propyl, and butyl chlorides, bromides and iodides; dialkyl sulfates like dimethyl and diethyl sulfate; and others.

It will also be recognized that compounds of the invention may possess asymmetric centres and are therefore capable of existing in more than one stereoisomeric form. The invention thus also relates to compounds in substantially pure isomeric form at one or more asymmetric centres eg., greater than about 90% ee, such as about 95% or 97% ee or greater than 99% ee, as well as mixtures, including racemic mixtures, thereof. Such isomers may be prepared by asymmetric synthesis, for example using chiral intermediates, or by chiral resolution. The compounds of the invention may exist as geometric isomers. The invention also relates to compounds in substantially pure cis (Z) or trans (E) or mixtures thereof.

Compounds of the Invention

In a first aspect of the present invention there is provided a compound of formula (I):

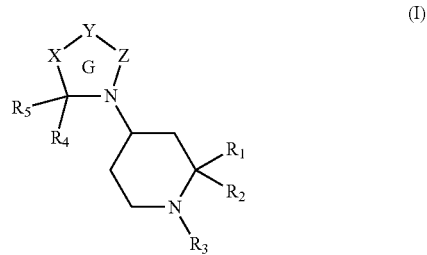

wherein Ring G is a 5 to 8 membered ring and

X is absent or is selected from —(CR$_6$R$_7$)$_n$—, —W—, —(CR$_6$R$_7$)$_m$—W—, —W—(CR$_6$R$_7$)$_m$— and —(CR$_6$R$_7$)$_p$—W—(CR$_6$R$_7$)$_p$—;

Y is —CR$_8$CR$_9$— wherein R$_8$ and R$_9$ together with the carbon atoms to which they are attached form an optionally substituted aromatic or heteroaromatic ring or ring system;

Z is absent or is selected from —CR$_4$R$_5$—, —CR$_6$R$_7$CR$_4$R$_5$— and —W—(CR$_4$R$_5$)—;

W is selected from —O—, —S—, —S(O)—, —S(O)$_2$—, —C(O)—, —NR$_{10}$—, —C(O)N(R$_{11}$)—, —N(R$_{11}$)C(O)—, —C(O)O—, —OC(O)—, —S(O)$_2$N(R$_{11}$)—, —N(R$_{11}$)S(O)$_2$—, —N(R$_{11}$)C(O)N(R$_{11}$)— and —N(R$_{11}$)S(O)$_2$N(R$_{11}$)—;

R$_1$ is selected from —CO$_2$H, —CH$_2$CO$_2$H, —C(O)C(O)OH, —CH$_2$OH, —C(O)NH$_2$, —CN, —CH$_2$C(O)NH$_2$, —CH$_2$CN, a carboxylic acid bioisostere and —CH$_2$carboxylic acid bioisostere;

R$_2$ is selected from hydrogen, alkyl, alkenyl, alkynyl, —C$_{1-6}$alkyleneR$_{12}$, —C$_{2-6}$alkenyleneR$_{12}$ and —C$_{2-6}$alkynyleneR$_{12}$;

R$_3$ is selected from —C(O)CH(aryl)(aryl) and —C(O)N(aryl)(aryl);

Each R$_4$ and R$_5$ are independently selected from hydrogen, alkyl, alkenyl, alkynyl, —OC(R$_{14}$)$_3$, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, —S(O)$_2$N(R$_{13}$)$_2$, —C(R$_{14}$)$_3$, cycloalkyl, cycloalkenyl, aryl, heterocyclyl and heteroaryl, or R$_4$ and R$_5$ taken together from a carbonyl group;

R$_6$ and R$_7$ are independently selected from hydrogen, alkyl, alkenyl, alkynyl, —OR$_{13}$, —SR$_{13}$, halo, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl, or R$_6$ and R$_7$ taken together form a carbonyl group;

R$_{10}$ is selected from hydrogen, alkyl, alkenyl, alkynyl, cycloalkyl, cycloalkenyl, aryl, heterocyclyl, heteroaryl, —C(R$_{14}$)$_3$, —C(O)R$_{13}$, —C(O)N(R$_{13}$)$_2$, —S(O)R$_{13}$, —S(O)$_2$R$_{13}$, —S(O)$_2$N(R$_{13}$)$_2$ and —CO$_2$R$_{13}$;

R$_{11}$ is selected from hydrogen and alkyl;

R$_{12}$ is selected from cycloalkyl, cycloalkenyl, aryl, heterocyclyl and heteroaryl;

Each R$_{13}$ is independently selected from hydrogen, alkyl, alkenyl, alkynyl, cycloalkyl, cycloalkenyl, aryl, heterocyclyl and heteroaryl;

Each R$_{14}$ is independently selected from hydrogen and halo;

n is selected from an integer from 1 to 4;
m is selected from an integer from 1 to 3;
p is selected from an integer of 1 or 2;
wherein each alkyl, alkenyl, alkynyl, cycloalkyl, cycloalkenyl, aryl, heterocyclyl and heteroaryl may be optionally substituted; or
a pharmaceutically acceptable salt thereof.

In particular embodiments of formula (I), one or more of the following applies:

Ring G is a 5 to 8 membered ring, especially a 7 membered ring;

X is absent or is selected from —(CR$_6$R$_7$)$_n$—, —W—, —(CR$_6$R$_7$)$_m$—W and —(CR$_6$R$_7$)$_p$—W—(CR$_6$R$_7$)$_p$—, especially —CR$_6$R$_7$—CR$_6$R$_7$—, —CR$_6$R$_7$—CR$_6$R$_7$—CR$_6$R$_7$—, —CR$_6$R$_7$—CR$_6$R$_7$—CR$_6$R$_7$—CR$_6$R$_7$—, —CR$_6$R$_7$—W—, —CR$_6$R$_7$CR$_6$R$_7$—W— and —CR$_6$R$_7$—W—CR$_6$R$_7$, more especially —CR$_6$R$_7$—CR$_6$R$_7$—, —CR$_6$R$_7$—CR$_6$R$_7$—CR$_6$R$_7$—, —CR$_6$R$_7$—CR$_6$R$_7$—CR$_6$R$_7$—CR$_6$R$_7$—, —CR$_6$R$_7$—W—, —CR$_6$R$_7$CR$_6$R$_7$—W— and —CR$_6$R$_7$—W—CR$_6$R$_7$, even more especially —CH$_2$CH$_2$—, —CH$_2$CH$_2$CH$_2$—, —CH$_2$CH$_2$CH$_2$CH$_2$—, —CH$_2$W—, —CH$_2$CH$_2$W—, —CH$_2$WCH$_2$—, for example —CH$_2$CH$_2$—, —CH$_2$CH$_2$CH$_2$—, —CH$_2$CH$_2$CH$_2$CH$_2$—, —CH$_2$CH$_2$O—, —CH$_2$C(O)NH—, —CH$_2$NHC(O)—, —CH$_2$CH$_2$C(O)NH—, —CH$_2$CH$_2$NHC(O)—, —CH$_2$C(O)NHCH$_2$—, —CH$_2$NHC(O)CH$_2$—, —CH$_2$S(O)$_2$NH—, —CH$_2$NHS(O)$_2$—, —CH$_2$CH$_2$S(O)$_2$NH—, —CH$_2$CH$_2$NHS(O)$_2$—, —CH$_2$S(O)$_2$NHCH$_2$— and —CH$_2$NHS(O)$_2$CH$_2$—, most especially —CH$_2$CH$_2$—, —CH$_2$CH$_2$CH$_2$—, —CH$_2$CH$_2$CH$_2$CH$_2$— and —CH$_2$CH$_2$O—;

Y is —CR$_8$CR$_9$— wherein R$_8$ and R$_9$ together with the carbon atoms to which they are attached form an optionally substituted five or six membered monocyclic or eight to ten membered bicyclic aromatic or heteroaromatic ring system. In particular embodiments, the aromatic or heteroaromatic ring system is selected from phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl, triazinyl, indanyl, indenyl, coumarinyl, benzofuranyl, benzothiophenyl, indolinyl, indolyl, isoindolyl, benzimidazolyl, benzo-1,3-dioxalanyl, benzo-1,4-dioxanyl, benzodithiolyl, benzodihydrodithiolyl, benzodithianyl, cyclopentyl[b]pyridinyl, indazolyl, benzoxazolyl, benzothiazolyl, naphthalenyl, tetrahydronaphthalenyl, benzopyranyl, quinolinyl, isoquinolinyl, quinazolinyl, cinnolinyl, quinoxalinyl, naphthyridinyl, phthalazinyl, benzoxazinyl, benzoxadiazinyl and pteridinyl, especially phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl and triazinyl, more especially phenyl, pyridinyl, thiophenyl, pyrrolyl pyrazolyl, imidazolyl, thiazolyl, isothiazolyl, pyridazinyl, pyrimidinyl and pyrazinyl, even more especially, phenyl, pyridinyl, thiophenyl and pyrrolyl, most especially phenyl, pyridinyl and thiophenyl, wherein each aromatic or heteroaromatic ring may be optionally substituted with one or more optional substituents. Particular optional substituents include —C$_{1-6}$alkyl, —C$_{1-6}$alkoxy, halo, —CN, —SO$_2$C$_{1-6}$alkyl, —C(R$_{14}$)$_3$ and —OC(R$_{14}$)$_3$, especially methyl, methoxy, fluoro, chloro, —CN, —SO$_2$CH$_3$, —CF$_3$ and OCF$_3$; more especially methyl, methoxy, fluoro and chloro and in which sulphur atoms may be optionally substituted with one or two carbonyl groups;

Z is absent or is selected from —CR$_4$R$_5$— and —CR$_6$R$_7$CR$_4$R$_5$—, especially absent or —CH$_2$— and —CH$_2$CH$_2$, most especially absent.

In particular embodiments X, Y and Z together are selected from —(CR$_6$R$_7$)$_n$CR$_8$CR$_9$—, —(CR$_6$R$_7$)$_n$WCR$_8$CR$_9$—, —(CR$_6$R$_7$)$_p$W(CR$_6$R$_7$)$_p$CR$_8$CR$_9$—, —(CR$_6$R$_7$)$_p$CR$_8$CR$_9$(CR$_6$R$_7$)$_p$— and —CR$_6$R$_7$—W—CR$_8$CR$_9$—CR$_4$R$_5$—, especially —CH$_2$CH$_2$CR$_8$CR$_9$—, —CH$_2$CH$_2$CH$_2$CR$_8$CR$_9$—, —CH$_2$CH$_2$CH$_2$CH$_2$CR$_8$CR$_9$—, —CH$_2$W—CR$_8$CR$_9$—, —CH$_2$CH$_2$WCR$_8$CR$_9$—, —CH$_2$WCH$_2$CR$_8$CR$_9$—, —CH$_2$CH$_2$CR$_8$CR$_9$CH$_2$—, —CH$_2$CR$_8$CR$_9$CH$_2$CH$_2$— and —CH$_2$WCR$_8$CR$_9$CH$_2$—, more especially —CH$_2$CH$_2$CR$_8$CR$_9$—, —CH$_2$CH$_2$CH$_2$CR$_8$CR$_9$—, —CH$_2$CH$_2$CH$_2$CH$_2$CR$_8$CR$_9$—, —CH$_2$CH$_2$OCR$_8$CR$_9$—, —CH$_2$OCH$_2$CR$_8$CR$_9$—, —CH$_2$CH$_2$NH—CR$_8$CR$_9$—, —CH$_2$CH$_2$N(CH$_3$)—CR$_8$R$_9$—, —CH$_2$NHCH$_2$CR$_8$CR$_9$—, —CH$_2$N(CH$_3$)CH$_2$CR$_8$CR$_9$—, —CH$_2$CH$_2$CR$_8$CR$_9$CH$_2$—, —CH$_2$CR$_8$CR$_9$CH$_2$—, —CH$_2$CR$_8$CR$_9$CH$_2$CH$_2$—, —CH$_2$OCR$_8$CR$_9$CH$_2$—, —CH$_2$NHCR$_8$CR$_9$CH$_2$— and —CH$_2$N(CH$_3$)CR$_8$CR$_9$CH$_2$—, most especially —CH$_2$CH$_2$CR$_8$CR$_9$—, —CH$_2$CH$_2$CH$_2$CR$_8$CR$_9$—, —CH$_2$CH$_2$CH$_2$CH$_2$CR$_8$CR$_9$—, —CH$_2$CH$_2$OCR$_8$CR$_9$, —CH$_2$OCH$_2$CR$_8$CR$_9$—, —CH$_2$CH$_2$NH—CR$_8$CR$_9$—, —CH$_2$CH$_2$N(CH$_3$)—CR$_8$R$_9$—, —CH$_2$NHCH$_2$CR$_8$CR$_9$—, —CH$_2$N(CH$_3$)CH$_2$CR$_8$CR$_9$—, —CH$_2$CH$_2$CR$_8$CR$_9$CH$_2$—, —CH$_2$CR$_8$CR$_9$CH$_2$—, —CH$_2$CR$_8$CR$_9$CH$_2$CH$_2$—, —CH$_2$OCR$_8$CR$_9$CH$_2$—, —CH$_2$NHCR$_8$CR$_9$CH$_2$— and —CH$_2$N(CH$_3$)CR$_8$CR$_9$CH$_2$—.

In particular embodiments, Ring G together with R$_8$ and R$_9$ is selected from one of the following ring systems:

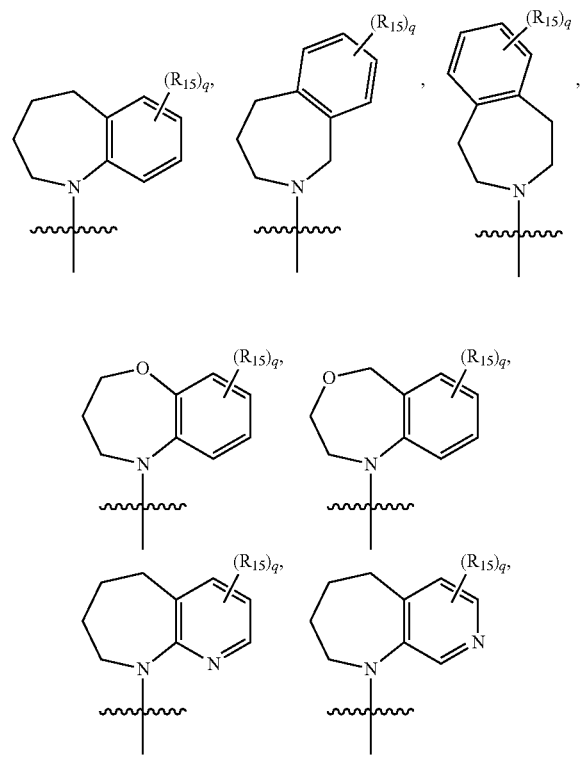

-continued
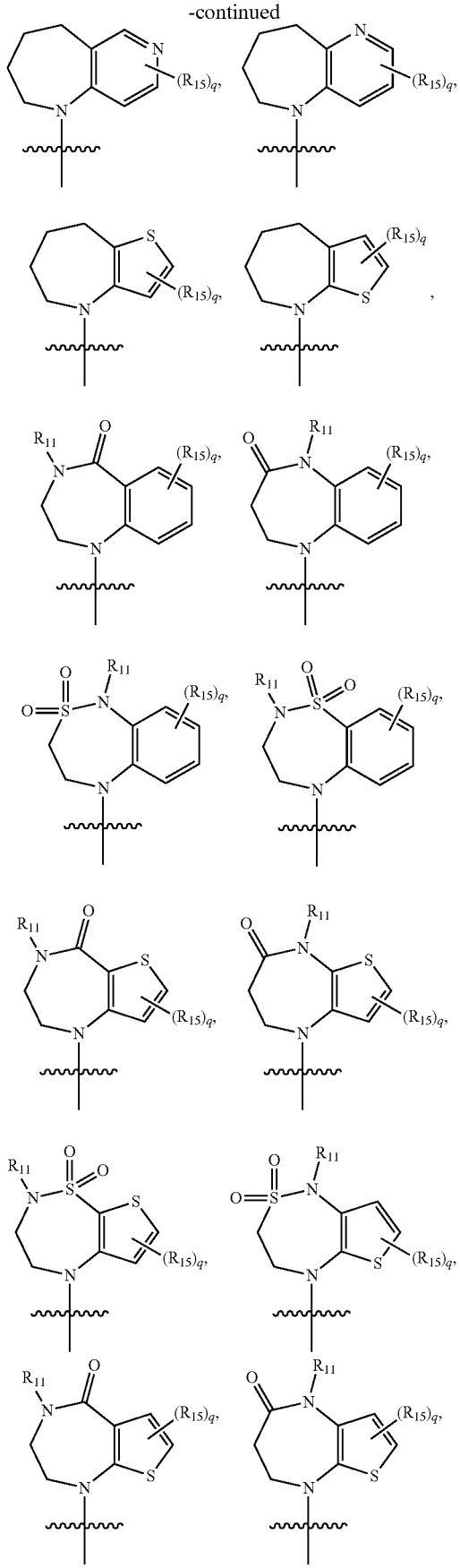
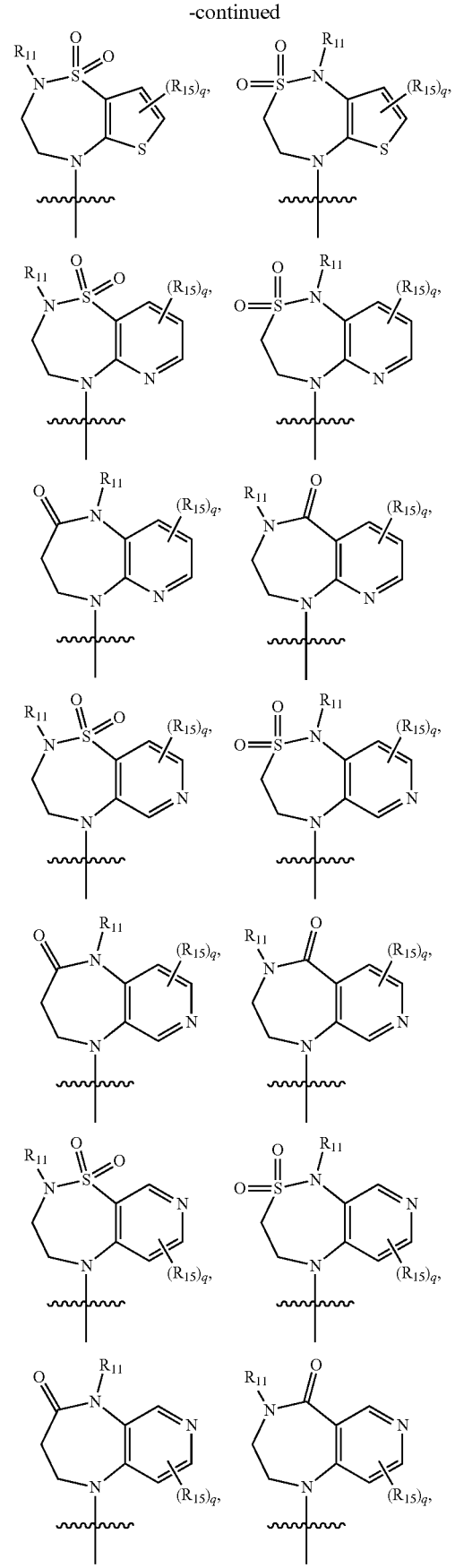

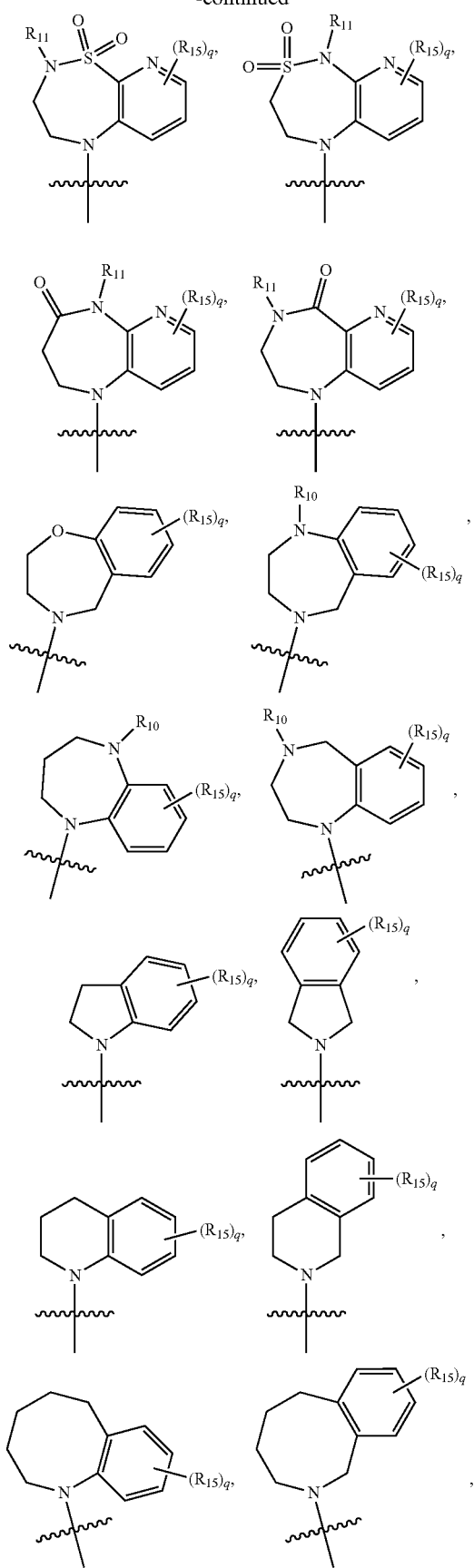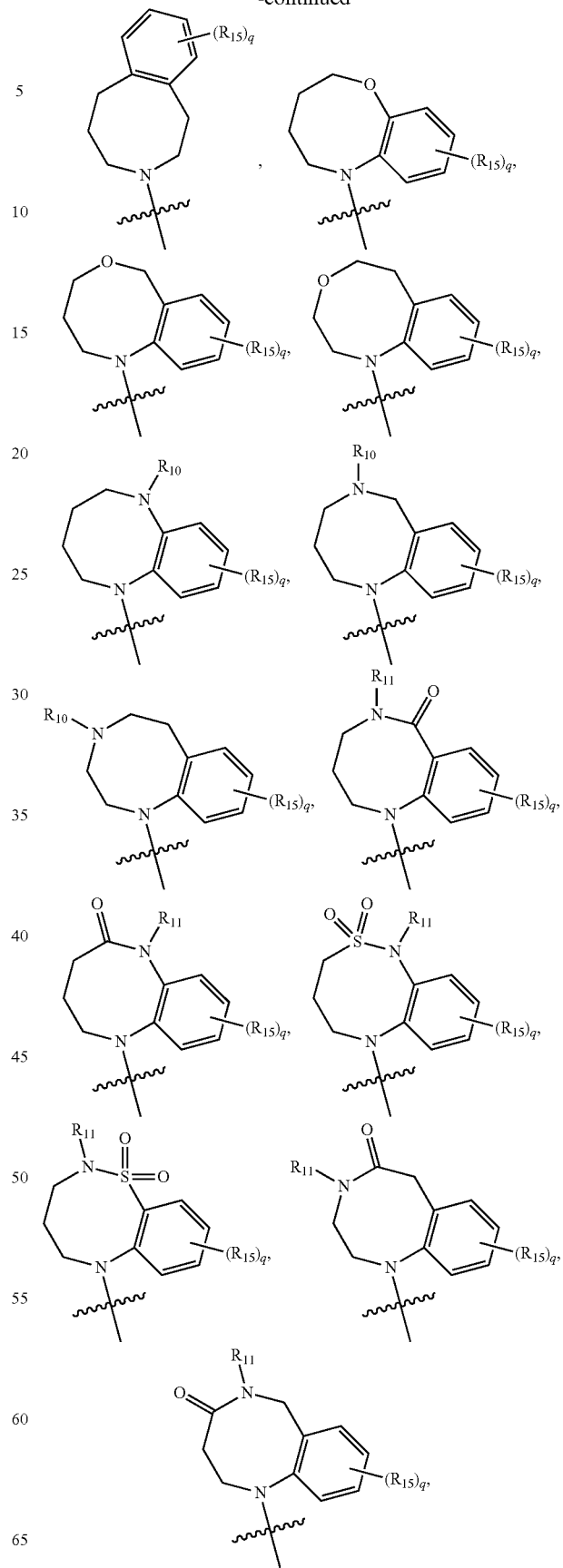

-continued
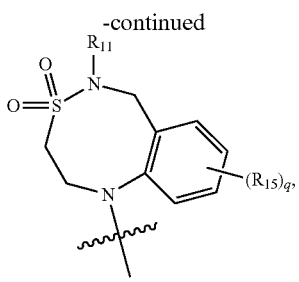
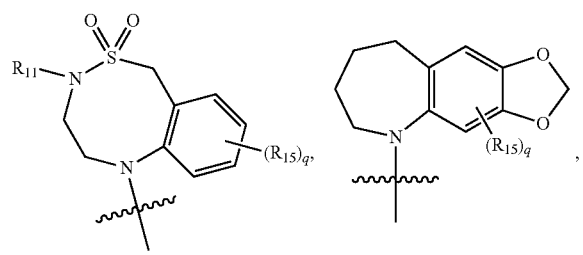
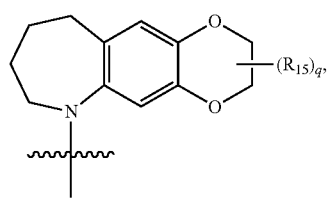
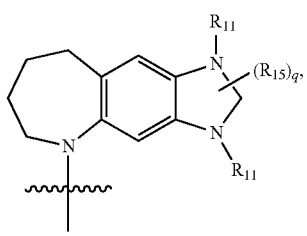
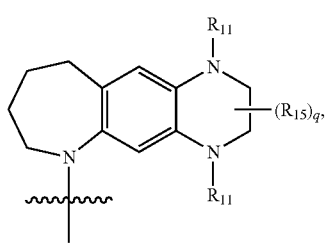
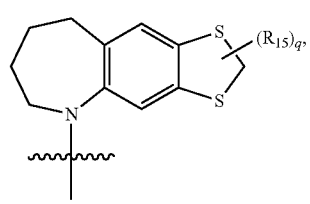
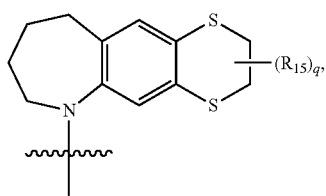
-continued
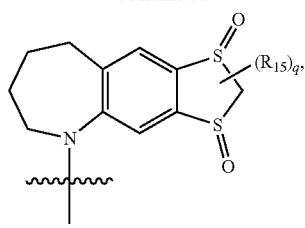
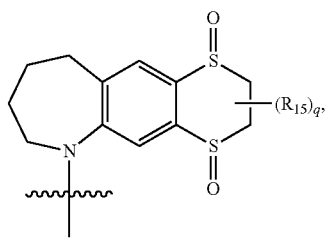
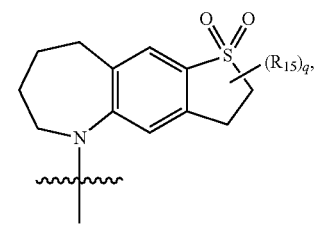
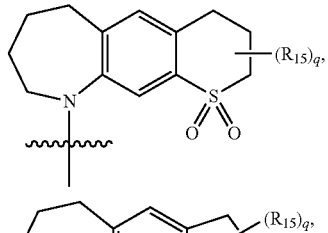
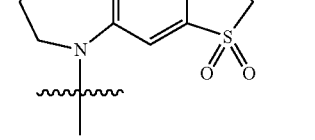
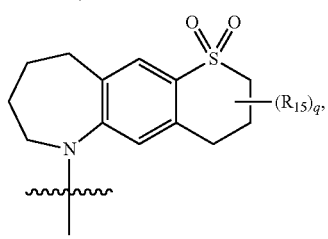
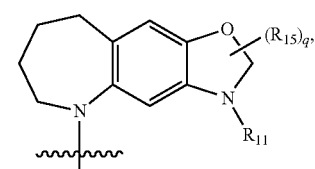
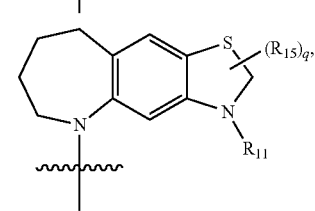

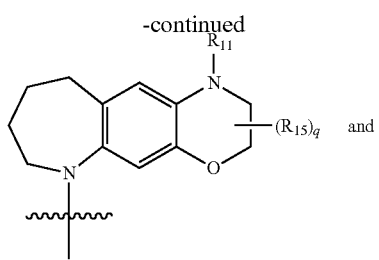
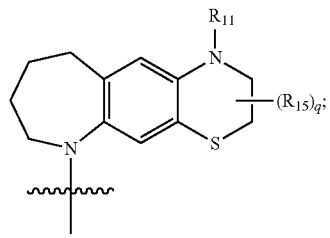
especially the following ring systems:
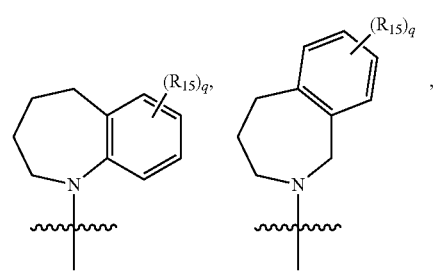
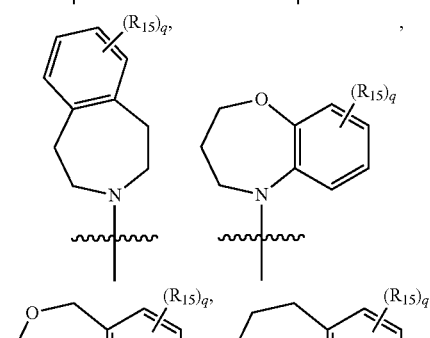
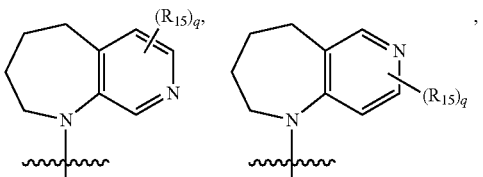
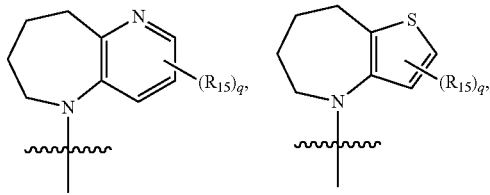
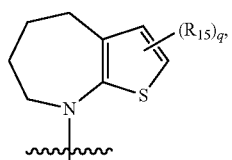 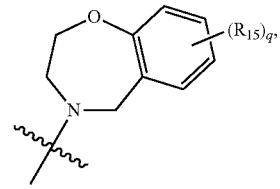
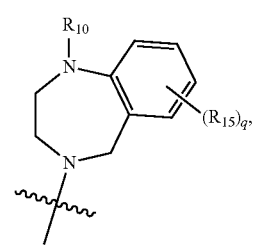 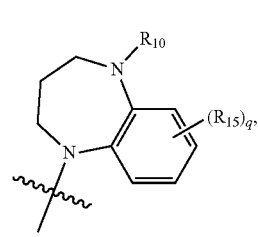
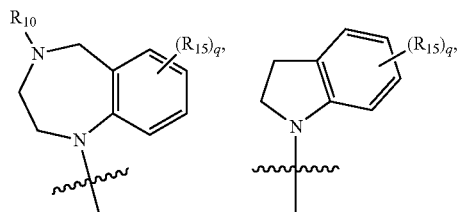
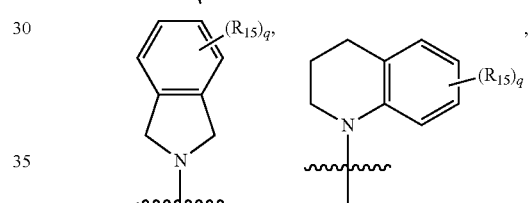
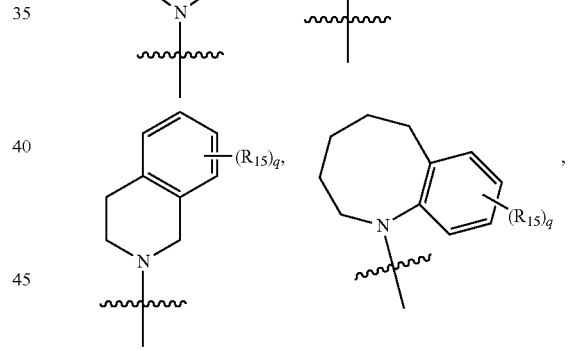
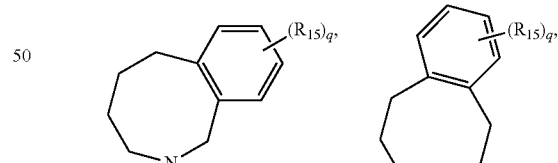

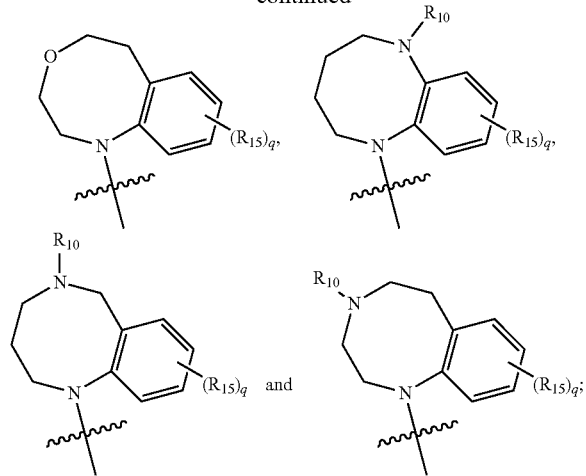

wherein each carbon atom in Ring G may be substituted with $R_4$, $R_5$, $R_6$ or $R_7$ as appropriate, each $R_{15}$ is independently selected from —$C_{1-6}$alkyl, —$C_{2-6}$alkenyl, —$C_{2-6}$alkynyl, —$OR_{13}$, —$SR_{13}$, halo, —CN, —$NO_2$, —$N(R_{13})_2$, —$CO_2R_{13}$, —$CON(R_{13})_2$, —$C(O)R_{13}$, —S(O)$_2R_{13}$, —S(O)$_2N(R_{13})_2$, —C($R_{14}$)$_3$, —OC($R_{14}$)$_3$, cycloalkyl, cycloalkenyl, aryl, heterocyclyl and heteroaryl and q is 0 or an integer from 1 to 4; and when q is less than the number of sites on the aryl or heteroaryl ring available for substitution, the carbon atoms not substituted with $R_{15}$ bear a hydrogen atom;

W is selected from —O—, —C(O)—, —S(O)$_2$—, —N($R_{10}$)—, —C(O)N($R_{11}$)—, —N($R_{11}$)C(O)—, —S(O)$_2$N($R_{11}$)— and —N($R_{11}$)S(O)$_2$—; especially —O— and —N($R_{10}$)—;

$R_1$ is selected from —$CO_2H$, —$CH_2CO_2H$, —C(O)C(O)OH, —C(O)$NH_2$, —CN, —C(O)NHSO$_2C_{1-6}$alkyl, —C(O)NHSO$_2C_{3-8}$cycloalkyl, —C(O)NHSO$_2$phenyl, —C(O)NHSO$_2$N($C_{1-6}$alkyl)$_2$, —C(O)NHSO$_2$N($C_{3-8}$cycloalkyl)$_2$, —C(O)NHSO$_2$N($C_{1-6}$alkyl)($C_{3-8}$cycloalkyl), —C(O)NHSO$_2$CF$_3$, tetrazole and tetrazolate, especially —$CO_2H$, —$CH_2CO_2H$, —C(O)$NH_2$, tetrazole, tetrazolate, —C(O)NHSO$_2C_{1-4}$alkyl, —C(O)NHSO$_2C_{3-6}$cycloalkyl, —C(O)NHSO$_2$phenyl, —C(O)NHSO$_2$CF$_3$, —C(O)NHSO$_2$N($C_{1-3}$alkyl)$_2$, —C(O)NHSO$_2$N($C_{1-3}$alkyl)($C_{3-6}$cycloalkyl) and —C(O)NHSO$_2$N($C_{3-6}$cycloalkyl)$_2$; more especially —$CO_2H$ and —$CONH_2$, most especially —$CO_2H$;

$R_2$ is selected from hydrogen, —$C_{1-6}$alkyl, —$C_{1-4}$alkylene$R_{12}$, —$C_{2-4}$alkenylene$R_{12}$ and —$C_{2-4}$alkynylene$R_{12}$, especially hydrogen and $C_{1-6}$alkyl, more especially hydrogen;

$R_3$ is selected from —C(O)CH(phenyl)(phenyl) and —C(O)N(phenyl)(phenyl), especially —C(O)CH(phenyl)(phenyl) wherein each phenyl group is independently optionally substituted with one or more optional substituents selected from —$C_{1-6}$alkyl, —OH, —$OC_{1-6}$alkyl, —CN, —$NO_2$, halo, —CF$_3$, —OCF$_3$, —CHF$_2$, —OCHF$_2$, —$CH_2F$, —$OCH_2F$, —$NH_2$, —NH($C_{1-6}$alkyl), —N($C_{1-6}$alkyl)$_2$, —$CO_2H$, —$CO_2C_{1-6}$alkyl, —$CONH_2$, —$SO_2C_{1-6}$alkyl and —$SO_2NH_2$;

$R_4$ and $R_5$ are each independently selected from hydrogen, —$C_{1-6}$alkyl, —$C_{2-6}$alkenyl, —$C_{2-6}$alkynyl, —OH, —CF$_3$, —CHF$_2$, —$CH_2F$, —OCF$_2$, —OCHF$_2$, —$OCH_2F$, —CN, —$NO_2$, —$NH_2$, —NH($C_{1-6}$alkyl), —N($C_{1-6}$alkyl)$_2$, —NH(aryl), —N($C_{1-6}$alkyl)(phenyl), —N(phenyl)$_2$, —$CO_2H$, —$CO_2C_{1-6}$alkyl, —$CO_2C_{2-6}$alkenyl, —$CO_2$phenyl, —C(O)$NH_2$, —C(O)NH$C_{1-6}$alkyl, —C(O)N($C_{1-6}$alkyl)$_2$, —C(O)$C_{1-6}$alkyl, —C(O)$C_{2-6}$alkenyl, —C(O)$C_{2-6}$alkynyl, —S(O)$_2C_{1-6}$alkyl, —S(O)$_2$aryl, —S(O)$_2NH_2$, —S(O)$_2$NH($C_{1-6}$alkyl) and —S(O)$_2$N($C_{1-6}$alkyl)$_2$, especially hydrogen, —$C_{1-6}$alkyl, —CF$_3$, —CHF$_2$, —$CH_2F$, halo, —OH, —OCF$_2$, —OCHF$_2$, —$OCH_2F$, —CN, —$NO_2$, —$NH_2$, —NH($C_{1-6}$alkyl), —N($C_{1-6}$alkyl)$_2$, —$CO_2H$, —$CO_2C_{1-6}$alkyl, —$CO_2NH_2$, —S(O)$_2C_{1-6}$alkyl, —S(O)$_2NH_2$, —S(O)NH($C_{1-6}$alkyl), —S(O)$_2$N($C_{1-6}$alkyl)$_2$ and —C(O)$C_{1-6}$alkyl, more especially hydrogen, —$C_{1-6}$alkyl, —CF$_3$, —CHF$_2$, —$CH_2F$, —OH, —OCF$_2$, —OCHF$_2$, —$OCH_2F$, —CN, —$NO_2$, —$NH_2$, —$CO_2H$ and —$CONH_2$, most especially hydrogen, —$C_{1-6}$alkyl and —CF$_3$; Each $R_6$ and $R_7$ are independently selected from hydrogen, —$C_{1-6}$alkyl, —$C_{2-6}$alkenyl, —$C_{2-6}$alkynyl, halo, —OH, —$OC_{1-6}$alkyl, —$OC_{2-6}$alkenyl, —$OC_{2-6}$alkynyl, —CN, —$NO_2$, —$NH_2$, —NH($C_{1-6}$alkyl), —N($C_{1-6}$alkyl)$_2$, —NH(aryl), —N($C_{1-6}$alkyl)(phenyl), —N(phenyl)$_2$, —$CO_2H$, —$CO_2C_{1-6}$alkyl, —$CO_2C_{2-6}$alkenyl, —CF$_3$, —CHF$_2$, —$CH_2F$, —OCF$_2$, —OCHF$_2$, —$OCH_2F$, —$CO_2$phenyl, —C(O)$NH_2$, —C(O)NH$C_{1-6}$alkyl, —C(O)N($C_{1-6}$alkyl)$_2$, —C(O)$C_{1-6}$alkyl, —C(O)$C_{2-6}$alkenyl, —C(O)$C_{2-6}$alkynyl, —S(O)$_2C_{1-6}$alkyl, —S(O)$_2$aryl, —S(O)$_2NH_2$, —S(O)$_2$NH($C_{1-6}$alkyl) and —S(O)$_2$N($C_{1-6}$alkyl)$_2$, especially —$C_{1-6}$alkyl, —CF$_3$, —CHF$_2$, —$CH_2F$, halo, —OH, —OCF$_2$, —OCHF$_2$, —$OCH_2F$, —$OC_{1-6}$alkyl, —CN, —$NO_2$, —$NH_2$, —NH($C_{1-6}$alkyl), —N($C_{1-6}$alkyl)$_2$, —$CO_2H$, —$CO_2C_{1-6}$alkyl, —$CO_2NH_2$, —S(O)$_2C_{1-6}$alkyl, —S(O)$_2NH_2$, —S(O)NH($C_{1-6}$alkyl), —S(O)$_2$N($C_{1-6}$alkyl)$_2$ and —C(O)$C_{1-6}$alkyl, more especially hydrogen, —$C_{1-6}$alkyl, —CF$_3$, —CHF$_2$, —$CH_2F$, halo, —OH, —OCF$_2$, —OCHF$_2$, —$OCH_2F$, —CN, —$NO_2$, —$NH_2$, —$CO_2H$ and —$CONH_2$, most especially hydrogen, —$C_{1-6}$alkyl, —CF$_3$ and halo; $R_{10}$ is selected from hydrogen, $C_{1-6}$alkyl, —C(O)$C_{1-6}$alkyl, —C(O)$C_{2-6}$alkenyl, —C(O)$C_{2-6}$alkynyl, —C(O)$C_{2-6}$alkynyl, —$CO_2H$, —$CO_2C_{1-6}$alkyl, —$CO_2C_{2-6}$alkenyl, —$CO_2C_{2-6}$alkynyl, —C(O)$NH_2$, —C(O)NH($C_{1-6}$alkyl), —C(O)NH($C_{2-6}$alkenyl), —C(O)NH($C_{2-6}$alkynyl), —C(O)N($C_{1-6}$alkyl)$_2$, —$SO_2C_{1-6}$alkyl, —$SO_2C_{2-6}$alkenyl, —$SO_2C_{2-6}$alkynyl, —$SO_2NH_2$, —$SO_2$NH($C_{1-6}$alkyl), —$SO_2$NH($C_{2-6}$alkenyl), —$SO_2$NH($C_{2-6}$alkynyl), —$SO_2$N($C_{1-6}$alkyl)$_2$, —$SO_2$CF$_3$, —$SO_2$NHC(O)$NH_2$, —$SO_2$NHC(O)NH($C_{1-6}$alkyl) and —$SO_2$NHC(O)N($C_{1-6}$alkyl)$_2$, especially hydrogen, $C_{1-6}$alkyl, —C(O)$C_{1-6}$alkyl, —$CO_2H$, —$CO_2C_{1-6}$alkyl, —C(O)$NH_2$, —C(O)NH($C_{1-6}$alkyl), —C(O)N($C_{1-6}$alkyl)$_2$, —$SO_2$alkyl, —$SO_2NH_2$, —$SO_2$NH($C_{1-6}$alkyl), —$SO_2$N($C_{1-6}$alkyl)$_2$, —$SO_2$CF$_3$, —$SO_2$NHC(O)$NH_2$, —$SO_2$NHC(O)NH($C_{1-6}$alkyl) and —$SO_2$NHC(O)N($C_{1-6}$alkyl)$_2$;

$R_{11}$ is selected from hydrogen or $C_{1-3}$alkyl, especially hydrogen and methyl;

$R_{12}$ is selected from cycloalkyl and aryl, especially $C_{3-6}$cycloalkyl and aryl, more especially cyclopropyl, cyclopentyl, cyclohexyl and phenyl;

Each $R_{13}$ is independently selected from hydrogen, $C_{1-6}$alkyl, $C_{3-6}$cycloalkyl, $C_{5-6}$cycloalkenyl and phenyl;

Each $R_{14}$ is independently selected from hydrogen and fluorine;

n is 1, 2 or 3, especially 2 or 3, more especially 3; and m is 1 or 2.

In particular embodiments, the stereogenic carbon atom bearing $R_1$ and $R_2$ substituents is in the S configuration.

In one embodiment, the compound of formula (I) is a compound of formula (II):

(II)

wherein

X is selected from —(CR$_6$R$_7$)$_n$—, —W—, —(CR$_6$R$_7$)$_m$—W—, —W—(CR$_6$R$_7$)$_m$— and —(CR$_6$R$_7$)$_p$—W—(CR$_6$R$_7$)$_p$—;

Ar is an aromatic or heteroaromatic ring or ring system;

R$_1$ is selected from —CO$_2$H, —CH$_2$CO$_2$H, —C(O)C(O)OH, —CH$_2$OH, —C(O)NH$_2$, —CN, —CH$_2$C(O)NH$_2$, —CH$_2$CN, a carboxylic acid bioisostere and —CH$_2$carboxylic acid bioisostere;

R$_2$ is selected from hydrogen, alkyl, alkenyl, alkynyl, —C$_{1-6}$alkyleneR$_{12}$, —C$_{2-6}$alkenyleneR$_{12}$ and —C$_{2-6}$alkynyleneR$_{12}$;

R$_3$ is selected from —C(O)CH(aryl)(aryl) and —C(O)N(aryl)(aryl);

Each R$_4$ and R$_5$ are independently selected from hydrogen, alkyl, alkenyl, alkynyl, —OC(R$_{14}$)$_3$, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, —S(O)$_2$N(R$_{13}$)$_2$, —C(R$_{14}$)$_3$, cycloalkyl, cycloalkenyl, aryl, heterocyclyl and heteroaryl, or R$_4$ and R$_5$ taken together from a carbonyl group;

R$_6$ and R$_7$ are independently selected from hydrogen, alkyl, alkenyl, alkynyl, —OR$_{13}$, —SR$_{13}$, halo, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl, or R$_6$ and R$_7$ taken together form a carbonyl group;

W is selected from —O—, —S—, —S(O)—, —S(O)$_2$—, —C(O)—, —NR$_{10}$—, —C(O)N(R$_{11}$)—, —N(R$_{11}$)C(O)—, —C(O)O—, —OC(O)—, —S(O)$_2$N(R$_{11}$)—, —N(R$_{11}$)S(O)$_2$—, —N(R$_{11}$)C(O)N(R$_{11}$)— and —N(R$_{11}$)S(O)$_2$N(R$_{11}$)—;

R$_{10}$ is selected from hydrogen, alkyl, alkenyl, alkynyl, cycloalkyl, cycloalkenyl, aryl, heterocyclyl, heteroaryl, —C(R$_{14}$)$_3$, —C(O)R$_{13}$, —C(O)N(R$_{13}$)$_2$, —S(O)R$_{13}$, —S(O)$_2$R$_{13}$, —S(O)$_2$N(R$_{13}$)$_2$ and —CO$_2$R$_{13}$;

R$_{11}$ is selected from hydrogen and alkyl;

R$_{12}$ is selected from cycloalkyl, cycloalkenyl, aryl, heterocyclyl and heteroaryl;

Each R$_{13}$ is independently selected from hydrogen, alkyl, alkenyl, alkynyl, cycloalkyl, cycloalkenyl, aryl, heterocyclyl and heteroaryl;

Each R$_{14}$ is independently selected from hydrogen and halo;

Each R$_{15}$ is independently selected from —C$_{1-6}$alkyl, —C$_{2-6}$alkenyl, —C$_{2-6}$alkynyl, —OR$_{13}$, —SR$_{13}$, halo, —CN, —NO$_2$, —N(R$_{13}$)$_2$, —CO$_2$R$_{13}$, —CON(R$_{13}$)$_2$, —C(O)R$_{13}$, —S(O)$_2$R$_{13}$, —S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl;

m is selected from an integer from 1 to 3;
n is selected from an integer from 1 to 4;
p is selected from an integer of 1 or 2; and
q is 0 or an integer of 1 to 4;

wherein each alkyl, alkenyl, alkynyl, cycloalkyl, cycloalkenyl, aryl, heterocyclyl and heteroaryl may be optionally substituted; or a pharmaceutically acceptable salt thereof.

In particular embodiments of formula (II), one or more of the following applies:

X is absent or is selected from —(CR$_6$R$_7$)$_n$—, —W—, —(CR$_6$R$_7$)$_m$—W— and —(CR$_6$R$_7$)$_p$—W—(CR$_6$R$_7$)$_p$—, especially —CR$_6$R$_7$—CR$_6$R$_7$—, —CR$_6$R$_7$—CR$_6$R$_7$—CR$_6$R$_7$—, —CR$_6$R$_7$—CR$_6$R$_7$—CR$_6$R$_7$—CR$_6$R$_7$—, —CR$_6$R$_7$—W—, —CR$_6$R$_7$CR$_6$R$_7$—W— and —CR$_6$R$_7$—W—CR$_6$R$_7$, more especially —CR$_6$R$_7$—CR$_6$R$_7$—, —CR$_6$R$_7$—CR$_6$R$_7$—CR$_6$R$_7$—, —CR$_6$R$_7$—CR$_6$R$_7$—CR$_6$R$_7$—CR$_6$R$_7$—, —CR$_6$R$_7$—W—, —CR$_6$R$_7$CR$_6$R$_7$—W— and —CR$_6$R$_7$—W—CR$_6$R$_7$, for example —CH$_2$CH$_2$—, —CH$_2$CH$_2$CH$_2$—, —CH$_2$CH$_2$CH$_2$CH$_2$—, —CH$_2$W—, —CH$_2$CH$_2$W—, —CH$_2$WCH$_2$—, even more especially —CH$_2$CH$_2$—, —CH$_2$CH$_2$CH$_2$—, —CH$_2$CH$_2$CH$_2$CH$_2$—, —CH$_2$CH$_2$O—, —CH$_2$C(O)NH—, —CH$_2$NHC(O)—, —CH$_2$CH$_2$C(O)NH—, —CH$_2$CH$_2$NHC(O)—, —CH$_2$C(O)NHCH$_2$—, —CH$_2$NHC(O)CH$_2$—, —CH$_2$S(O)$_2$NH—, —CH$_2$NHS(O)$_2$—, —CH$_2$CH$_2$S(O)$_2$NH—, —CH$_2$CH$_2$NHS(O)$_2$—, —CH$_2$S(O)$_2$NHCH$_2$— and —CH$_2$NHS(O)$_2$CH$_2$— most especially —CH$_2$CH$_2$—, —CH$_2$CH$_2$CH$_2$—, —CH$_2$CH$_2$CH$_2$CH$_2$— and —CH$_2$CH$_2$O—;

Ar is a 5 or 6 membered monocyclic or 8 to 10 membered bicyclic aromatic or heteroaromatic ring system, for example one selected from phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl, triazinyl, indanyl, indenyl, coumarinyl, benzofuranyl, benzothiophenyl, indolinyl, indolyl, isoindolyl, benzimidazolyl, benzo-1,3-dioxalanyl, benzo-1,4-dioxanyl, benzodithiolyl, benzodihydrodithiolyl, benzodithianyl, cyclopentyl[b]pyridinyl, indazolyl, benzoxazolyl, benzothiazolyl, naphthalenyl, tetrahydronaphthalenyl, benzopyranyl, quinolinyl, isoquinolinyl, quinazolinyl, cinnolinyl, quinoxalinyl, naphthyridinyl, phthalazinyl, benzoxazinyl, benzoxadiazinyl and pteridinyl, especially phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl and triazinyl, more especially phenyl, pyridinyl, thiophenyl, pyrrolyl pyrazolyl, imidazolyl, thiazolyl, isothiazolyl, pyridazinyl, pyrimidinyl and pyrazinyl, even more especially, phenyl, pyridinyl, thiophenyl and pyrrolyl, most especially phenyl, pyridinyl and thiophenyl. In some embodiments Ar is an aryl or heteroaryl ring system selected from one of the following:

-continued
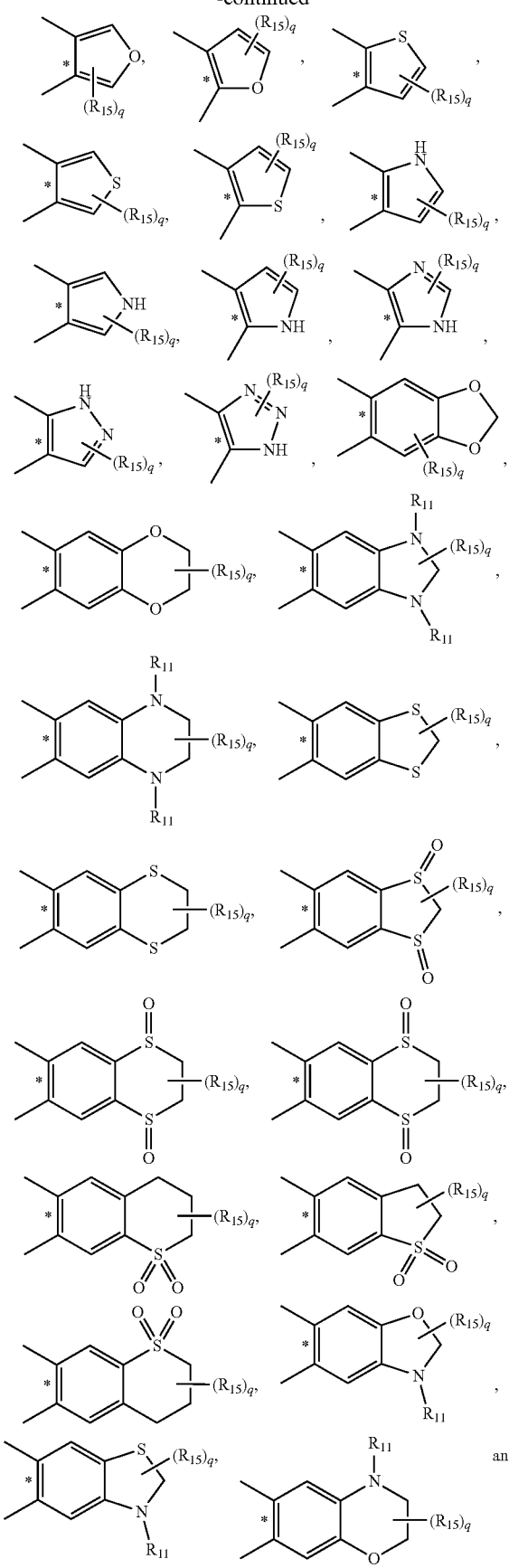
-continued
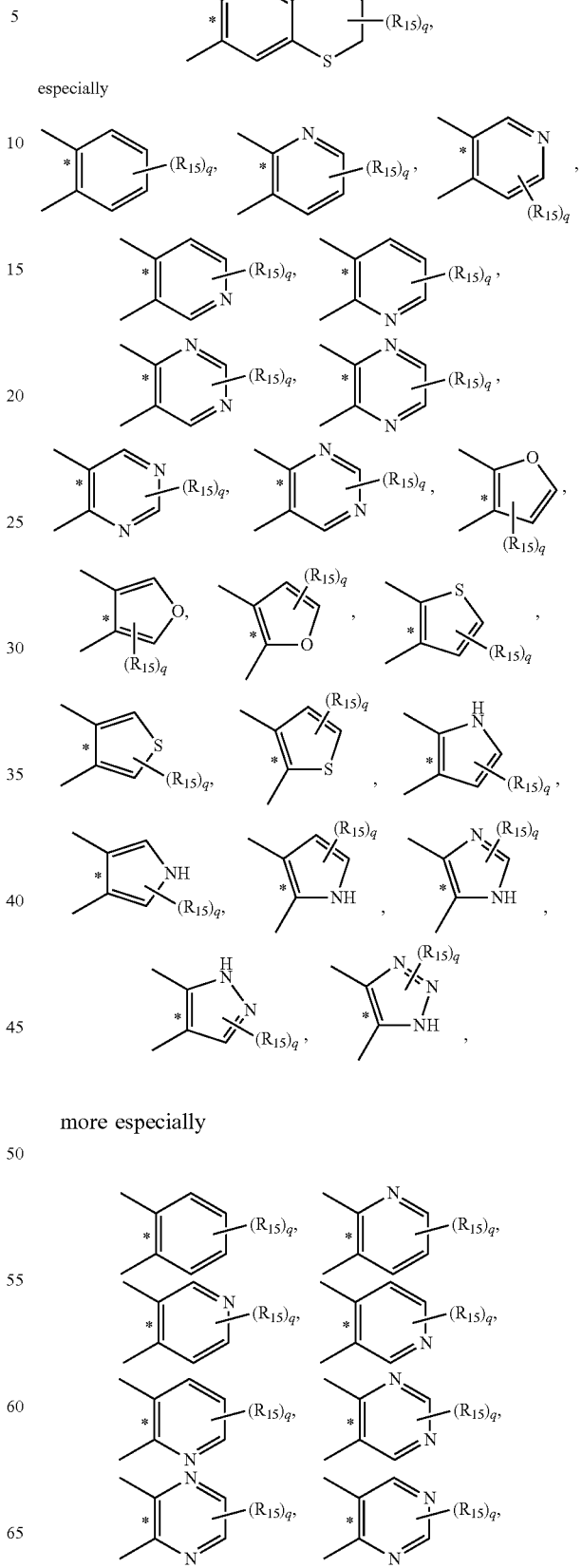
especially
more especially

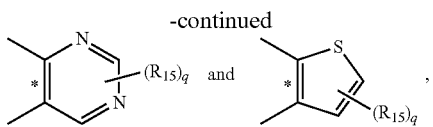

most especially

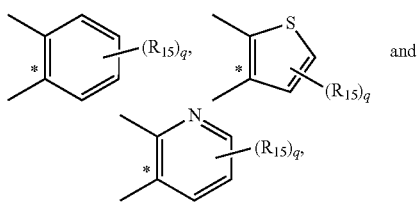

wherein * represents the common bond with Ring G; and when q is less than the number of sites on the aryl or heteroaryl ring available for substitution, the carbon atoms not substituted with $R_{15}$ bear a hydrogen atom;

$R_1$ is selected from —$CO_2H$, —$CH_2CO_2H$, —C(O)C(O) OH, —C(O)$NH_2$, —CN, —C(O)$NHSO_2C_{1-6}$alkyl, —C(O) $NHSO_2C_{3-8}$cycloalkyl, —C(O)$NHSO_2$phenyl, —C(O) $NHSO_2N(C_{1-6}$alkyl$)_2$, —C(O)$NHSO_2N(C_{3-8}$cycloalkyl$)_2$, —C(O)$NHSO_2N(C_{1-6}$alkyl)($C_{3-8}$cycloalkyl), —C(O) $NHSO_2CF_3$, tetrazole and tetrazolate, especially —$CO_2H$, —$CH_2CO_2H$, —C(O)$NH_2$, tetrazole, tetrazolate, —C(O) $NHSO_2C_{1-4}$alkyl, —C(O)$NHSO_2C_{3-6}$cycloalkyl, —C(O) $NHSO_2$phenyl, —C(O)$NHSO_2CF_3$, —C(O)$NHSO_2N(C_{1-3}$alkyl$)_2$, —C(O)$NHSO_2N(C_{1-3}$alkyl)($C_{3-6}$cycloalkyl) and —C(O)$NHSO_2N(C_{3-6}$cycloalkyl$)_2$; more especially —$CO_2H$ and —$CONH_2$, most especially —$CO_2H$;

$R_2$ is selected from hydrogen, —$C_{1-6}$alkyl, —$C_{1-4}$alkylene$R_{12}$, —$C_{2-4}$alkenylene$R_{12}$ and —$C_{2-4}$alkynylene$R_{12}$, especially hydrogen and $C_{1-6}$alkyl, more especially hydrogen;

$R_3$ is selected from —C(O)CH(phenyl)(phenyl) and —C(O)N(phenyl)(phenyl), especially —C(O)CH(phenyl) (phenyl) wherein each phenyl group is independently optionally substituted with one or more optional substituents selected from —$C_{1-6}$alkyl, —OH, —$OC_{1-6}$alkyl, —CN, —$NO_2$, halo, —$CF_3$, —$OCF_3$, —$CHF_2$, —$OCHF_2$, —$CH_2F$, —$OCH_2F$, —$NH_2$, —NH($C_{1-6}$alkyl), —N($C_{1-6}$alkyl$)_2$, —$CO_2H$, —$CO_2C_{1-6}$alkyl, —$CONH_2$, —$SO_2C_{1-6}$alkyl and —$SO_2NH_2$;

$R_4$ and $R_5$ are each independently selected from hydrogen, —$C_{1-6}$alkyl, —$C_{2-6}$alkenyl, —$C_{2-6}$alkynyl, —OH, —$CF_3$, —$CHF_2$, —$CH_2F$, —$OCF_2$, —$OCHF_2$, —$OCH_2F$, —CN, —$NO_2$, —$NH_2$, —NH($C_{1-6}$alkyl), —N($C_{1-6}$alkyl$)_2$, —NH (aryl), —N($C_{1-6}$alkyl)(phenyl), —N(phenyl$)_2$, —$CO_2H$, —$CO_2C_{1-6}$alkyl, —$CO_2C_{2-6}$alkenyl, —$CO_2$phenyl, —C(O) $NH_2$, —C(O)$NHC_{1-6}$alkyl, —C(O)N($C_{1-6}$alkyl$)_2$, —C(O) $C_{1-6}$alkyl, —C(O)$C_{2-6}$alkenyl, —C(O)$C_{2-6}$alkynyl, —S (O)$_2C_{1-6}$alkyl, —S(O)$_2$aryl, —S(O)$_2NH_2$, —S(O)$_2$NH ($C_{1-6}$alkyl) and —S(O)$_2$N($C_{1-6}$alkyl$)_2$, especially hydrogen, —$C_{1-6}$alkyl, —$CF_3$, —$CHF_2$, —$CH_2F$, halo, —OH, —$OCF_2$, —$OCHF_2$, —$OCH_2F$, —CN, —$NO_2$, —$NH_2$, —NH($C_{1-6}$alkyl), —N($C_{1-6}$alkyl$)_2$, —$CO_2H$, —$CO_2$ $C_{1-6}$alkyl, —$CO_2NH_2$, —S(O)$_2C_{1-6}$alkyl, —S(O)$_2NH_2$, —S(O)NH($C_{1-6}$alkyl), —S(O)$_2$N($C_{1-6}$alkyl$)_2$ and —C(O) $C_{1-6}$alkyl, more especially hydrogen, —$C_{1-6}$alkyl, —$CF_3$, —$CHF_2$, —$CH_2F$, —OH, —$OCF_2$, —$OCHF_2$, —$OCH_2F$, —CN, —$NO_2$, —$NH_2$, —$CO_2H$ and —$CONH_2$, most especially hydrogen, —$C_{1-6}$alkyl and —$CF_3$; Each $R_6$ and $R_7$ are independently selected from hydrogen, —$C_{1-6}$alkyl, —$C_{2-6}$alkenyl, —$C_{2-6}$alkynyl, halo, —OH, —$OC_{1-6}$alkyl, —$OC_{2-6}$alkenyl, —$OC_{2-6}$alkynyl, —CN, —$NO_2$, —$NH_2$, —NH($C_{1-6}$alkyl), —N($C_{1-6}$alkyl$)_2$, —NH(aryl), —N ($C_{1-6}$alkyl)(phenyl), —N(phenyl$)_2$, —$CO_2H$, —$CO_2$ $C_{1-6}$alkyl, —$CO_2C_{2-6}$alkenyl, —$CF_3$, —$CHF_2$, —$CH_2F$, —$OCF_2$, —$OCHF_2$, —$OCH_2F$, —$CO_2$phenyl, —C(O)$NH_2$, —C(O)$NHC_{1-6}$alkyl, —C(O)N($C_{1-6}$alkyl$)_2$, —C(O) $C_{1-6}$alkyl, —C(O)$C_{2-6}$alkenyl, —C(O)$C_{2-6}$alkynyl, —S (O)$_2C_{1-6}$alkyl, —S(O)$_2$aryl, —S(O)$_2NH_2$, —S(O)$_2$NH ($C_{1-6}$alkyl) and —S(O)$_2$N($C_{1-6}$alkyl$)_2$, especially hydrogen, —$C_{1-6}$alkyl, —$CF_3$, —$CHF_2$, —$CH_2F$, halo, —OH, —$OCF_2$, —$OCHF_2$, —$OCH_2F$, —$OC_{1-6}$alkyl, —CN, —$NO_2$, —$NH_2$, —NH($C_{1-6}$alkyl), —N($C_{1-6}$alkyl$)_2$, —$CO_2H$, —$CO_2C_{1-6}$alkyl, —$CO_2NH_2$, —S(O)$_2C_{1-6}$alkyl, —S(O)$_2NH_2$, —S(O)NH($C_{1-6}$alkyl), —S(O)$_2$N($C_{1-6}$alkyl$)_2$ and —C(O)$C_{1-6}$alkyl, more especially hydrogen, —$C_{1-6}$alkyl, —$CF_3$, —$CHF_2$, —$CH_2F$, halo, —OH, —$OCF_2$, —$OCHF_2$, —$OCH_2F$, —CN, —$NO_2$, —$NH_2$, —$CO_2H$ and —$CONH_2$, most especially hydrogen, —$C_{1-6}$alkyl, —$CF_3$ and halo;

$R_{10}$ is selected from hydrogen, $C_{1-6}$alkyl, —C(O) $C_{1-6}$alkyl, —C(O)$C_{2-6}$alkenyl, —C(O)$C_{2-6}$alkynyl, —C(O) $C_{2-6}$alkynyl, —$CO_2H$, —$CO_2C_{1-6}$alkyl, —$CO_2C_{2-6}$alkenyl, —$CO_2C_{2-6}$alkynyl, —C(O)$NH_2$, —C(O)NH($C_{1-6}$alkyl), —C(O)NH($C_{2-6}$alkenyl), —C(O)NH($C_{2-6}$alkynyl), —C(O) N($C_{1-6}$alkyl$)_2$, —$SO_2C_{1-6}$alkyl, —$SO_2C_{2-6}$alkenyl, —$SO_2C_{2-6}$alkynyl, —$SO_2NH_2$, —$SO_2$NH($C_{1-6}$alkyl), —$SO_2$NH($C_{2-6}$alkenyl), —$SO_2$NH($C_{2-6}$alkynyl), —$SO_2$N ($C_{1-6}$alkyl$)_2$, —$SO_2CF_3$, —$SO_2$NHC(O)$NH_2$, —$SO_2$NHC (O)NH($C_{1-6}$alkyl) and —$SO_2$NHC(O)N($C_{1-6}$alkyl$)_2$, especially hydrogen, $C_{1-6}$alkyl, —C(O)$C_{1-6}$alkyl, —$CO_2H$, —$CO_2C_{1-6}$alkyl, —C(O)$NH_2$, —C(O)NH($C_{1-6}$alkyl), —C(O)N($C_{1-6}$alkyl$)_2$, —$SO_2$alkyl, —$SO_2NH_2$, —$SO_2$NH ($C_{1-6}$alkyl), —$SO_2$N($C_{1-6}$alkyl$)_2$, —$SO_2CF_3$, —$SO_2$NHC (O)$NH_2$, —$SO_2$NHC(O)NH($C_{1-6}$alkyl) and —$SO_2$NHC(O) N($C_{1-6}$alkyl$)_2$;

$R_{11}$ is selected from hydrogen or $C_{1-3}$alkyl, especially hydrogen and methyl;

$R_{12}$ is selected from cycloalkyl and aryl, especially $C_{3-6}$cycloalkyl and aryl, more especially cyclopropyl, cyclopentyl, cyclohexyl and phenyl;

Each $R_{13}$ is independently selected from hydrogen, $C_{1-6}$alkyl, $C_{3-6}$cycloalkyl, $C_{5-6}$cycloalkenyl and phenyl;

Each $R_{14}$ is independently selected from hydrogen and fluorine;

Each $R_{15}$ is independently selected from —$C_{1-6}$alkyl, —$CF_3$, —$CHF_2$, —$CH_2F$, halo, —OH, —$OC_{1-6}$alkyl, —$OCF_2$, —$OCHF_2$, —$OCH_2F$, —$CO_2H$, —$SO_2H$, —S (O)$_2C_{1-6}$alkyl, —S(O)$_2$aryl, —S(O)$_2NH_2$, —S(O)$_2$NH ($C_{1-6}$alkyl), —S(O)$_2$N($C_{1-6}$alkyl$)_2$, —CN, —$NO_2$, —$NH_2$, —NH($C_{1-6}$alkyl) and —N($C_{1-6}$alkyl$)_2$, especially —$C_{1-6}$alkyl, —$CF_3$, —$CHF_2$, —$CH_2F$, halo, —$OC_{1-6}$alkyl, —$OCF_2$, —$OCHF_2$, —$OCH_2F$, —S(O)$_2C_{1-6}$alkyl, —S (O)$_2$aryl, —S(O)$_2NH_2$, —S(O)$_2$NH($C_{1-6}$alkyl), —S(O)$_2$N ($C_{1-6}$alkyl$)_2$ and —CN; especially —$C_{1-6}$alkyl, —$C_{1-6}$alkoxy, halo, —C($R_{14})_3$ and —OC($R_{14})_3$, especially methyl, methoxy, fluoro, chloro, —CN, —$SO_2CH_3$, —$CF_3$ and $OCF_3$;

more especially methyl, methoxy and fluoro;

n is 1, 2 or 3, especially 2 or 3, more especially 3;

m is 1 or 2;

q is 0 or 1 to 3, especially 0 or 1 or 2, more especially 0 or 1.

Particular compounds of formula (I) and (II) are shown in Tables 1 and 2 below:

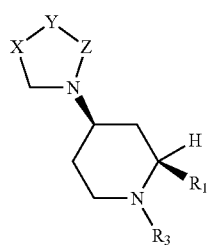

TABLE 1

| Compound | X | Y | Z | R1 | R3 |
|---|---|---|---|---|---|
| 1 | —CH$_2$CH$_2$—O— | 2,5-diF-4-Me-phenyl (F, F positions with methyl) | absent | —CO$_2$H | —C(O)CH(phenyl)$_2$ |
| 2 | —CH$_2$CH$_2$—O— | 4-F-2-Me-phenyl | absent | —CO$_2$H | —C(O)CH(phenyl)$_2$ |
| 3 | —CH$_2$CH$_2$—O— | 4-F-3-Me-phenyl | absent | —CO$_2$H | —C(O)CH(phenyl)$_2$ |
| 4 | —CH$_2$CH$_2$—O— | 2,3-diMe-phenyl | absent | —CO$_2$H | —C(O)CH(phenyl)$_2$ |
| 5 | —CH$_2$CH$_2$CH$_2$— | 2-OCH$_3$-4,5-diMe-phenyl | absent | —CO$_2$H | —C(O)CH(phenyl)$_2$ |
| 6 | —CH$_2$CH$_2$CH$_2$— | 2,3-diMe-phenyl | absent | —CO$_2$H | —C(O)CH(phenyl)$_2$ |
| 7 | —CH$_2$CH$_2$CH$_2$— | 2,5-diF-3,4-diMe-phenyl | absent | —CO$_2$H | —C(O)CH(phenyl)$_2$ |
| 8 | —CH$_2$CH$_2$CH$_2$— | 4-F-2,3-diMe-phenyl | absent | —CO$_2$H | —C(O)CH(phenyl)$_2$ |
| 9 | —CH$_2$CH$_2$CH$_2$— | 2-F-4,5-diMe-phenyl | absent | —CO$_2$H | —C(O)CH(phenyl)$_2$ |

TABLE 2

| Compound | X | Y | Z | R1 | R3 |
|---|---|---|---|---|---|
| 10 | —CH$_2$CH$_2$CH$_2$— | 2-F-4,5-diMe-phenyl | absent | —CO$_2$H | —C(O)CH(phenyl)$_2$ |

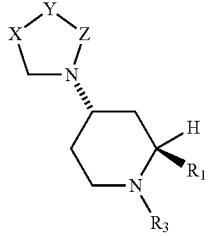

In particular embodiments, the compound of formulae (I) or (II) is one of compounds 1 to 6, 9 and 10, more especially compounds 1, 2, 3, 4 and 5, more especially compounds 1, 2 and 5.

In some embodiments, the compounds of formula (I) are selective AT$_2$ receptor antagonists. In particular embodiments, the selective AT$_2$ receptor antagonists have an IC$_{50}$ at the AT$_2$ receptor of ≤100 nM and an IC$_{50}$ at the AT$_1$ receptor of >100,000 nM (10 μM).

The compounds of the invention are made by methods known in the art from commercially available starting materials.

For preparation of piperidine derivatives, commercially available starting materials may be used, such as (S)-1-tert-butyl 2-methyl 4-oxopiperidine-1,2-carboxylic acid and (2S, 4R)-methyl 4-hydroxypiperidine-2-carboxylate hydrochloride.

R$_2$ may be introduced by removing the hydrogen α- to the carboxylic acid or ester with a suitable base and alkylating with a suitable alkylating agent, such as an alkylhalide.

R$_3$ may be introduced either before or after the introduction of the nitrogen-containing heterocyclic group. If the nitrogen-containing heterocyclic group is introduced prior to the introduction of $R_3$, it may be necessary to protect the ring nitrogen bearing $R_3$ during the amination reaction. Suitable nitrogen protecting groups are known in the art, for example, in Greene & Wutz, Protective Groups in Organic Synthesis, Third Edition, John Wiley & Sons, 1999. A suitable nitrogen protecting group is t-butoxycarbonyl (Boc).

$R_3$ may be introduced using an acid chloride such as $Ph_2CHC(O)Cl$, in the presence of base, such as $NaHCO_3$ or diisopropylethylamine.

Alternatively, $R_3$ may be introduced by amide formation with a suitable carboxylic acid and the ring nitrogen. Amide formation is well known in the art and may involve the activation of the carboxylic acid, for example, the carboxy group is activated by formation of an acid chloride, carbodiimide, triazole or a uronium or phosphonium salt of a non-nucleophilic anion. Suitable activating groups are well known in the art including dicyclohexylcarbodiimide (DCC), diisopropylcarbodiimide (DIC), 1-ethyl-3-(dimethylaminopropyl)carbodiimide (EDCI), 1-hydroxybenzotriazole (HOBt), 1-hydroxy-7-aza-benzotriazole (HOAt), ethyl-2-cyano-2-cyano-2-(hydroxyimino)acetate (Oxyma Pure), O-benzotriazole-N,N,N',N'-tetramethyluronium hexafluorophosphate (HBTU), O-(7-azabenzotriazol-1-yl)-N,N,N',N'-tetramethyluronium hexafluorophosphate (HATU), O-(6-chloro-1H-benzotriazol-1-yl)-1,1,3,3-tetramethyluronium tetrafluorophosphate (HCTU), O-benzotriazol-1-yl-N,N,N'N'-tetramethyluronium tetrafluoroborate (TBTU), (benzotriazol-1-yloxy)tripyrrolidinophosphonium hexafluorophosphate (PyBOP); (benzotriazol-1-yloxy)-tris-(dimethylamino)phosphonium hexafluorophosphate (BOP), (1-cyano-2-ethoxy-2-oxoethylidenaminooxy)-dimethylamino-morpholino-carbenium hexafluorophosphate (COMU) and O-[(ethoxycarbonyl)-cyanomethyleneamino]-N,N,N',N'-tetramethyluronium tetrafluoroborate (TOTU).

The N-heterocycle (Ring G) may be introduced onto the piperidine ring, before or after the introduction of $R_3$ and in which $R_1$ is optionally protected, where the piperidine ring is a 4-oxo-piperidine ring. The nitrogen heterocycle and oxo-piperidine are combined and acidified, for example with acetic acid. Subsequently, a borate, such as tetramethylammonium triacetoxyhydroborate, is added under an inert atmosphere.

Alternatively, N-containing heterocycle may be introduced by methods known in the art (for example, Reger et al., 2010). For example, 4-hydroxypiperidine derivatives, optionally with a carboxy protecting group, are treated with an anhydride such as triflic anhydride and a base such as diisopropylethylamine in dichloromethane, followed by treatment at −30° C. with the desired N-containing heterocycle with warming to room temperature.

Subsequently, if necessary, $R_1$ carboxylic acid may be deprotected, for example with base such as LiOH, and $R_3$ may be introduced. $R_1$ and $R_3$ may also be further derivatized if required.

In some instances where the N-containing heterocyclic ring (Ring G) is not commercially available, this ring or group may be made by known methods. For example, substituted benzo[b]azepines may be prepared from an appropriately substituted 3,4-dihydronaphthalene-1-(2H)-one by reaction with hydroxylamine hydrochloride in the presence of pyridine to provide an oxime followed by reduction and rearrangement, for example with DIBAL and treatment with NaF and water. Substituted benzooxazepines may be prepared from appropriately substituted phenols by treatment with 3-halopropionic acid and cyclization in the presence of triflic acid to give a substituted chroman-4-one, which may be subsequently treated with hydroxylamine hydrochloride and DIBAL as described above to form the substituted benzo[b][1,4]oxazepine.

Methods of the Invention

In one aspect of the present invention, there is provided a method of treating or preventing the symptoms of a neuropathic condition in a subject comprising administering a compound of formula (I) or a pharmaceutically acceptable salt thereof.

The compounds of formula (I) are effective in the prevention or attenuation of the symptoms of neuropathic conditions including primary and secondary neuropathic conditions. In accordance with the present invention, the compounds of formula (I) can act to treat, prevent or attenuate one or more symptoms associated with neuropathic conditions including, but not limited to, hyperesthesia, hyperalgesia, allodynia and/or spontaneous burning pain. In some embodiments, the compound of formula (I) is used to prevent or attenuate one or more symptoms associated with peripheral neuropathic conditions, illustrative examples of which include numbness, weakness, burning pain, shooting pain, and loss of reflexes. The pain may be severe and disabling. In some embodiments, the symptom, which is the subject of the prevention and/or attenuation, is neuropathic pain. Accordingly, in a related aspect, the invention provides methods for preventing and/or attenuating neuropathic pain in an individual, comprising administering to the individual a pain-preventing or -attenuating effective amount of an $AT_2$ receptor antagonist, which is suitably in the form of a pharmaceutical composition.

There are many possible causes of neuropathy and neuropathic pain and it will be understood that the present invention contemplates the treatment or prevention of symptoms of any neuropathic condition regardless of the cause. In some embodiments, the neuropathic conditions are a result of diseases of the nerves (primary neuropathy) and neuropathy that is caused by systemic disease (secondary neuropathy) such as but not limited to: diabetic neuropathy; Herpes Zoster (shingles)-related neuropathy; uremia-associated neuropathy; amyloidosis neuropathy; HIV sensory neuropathies; hereditary motor and sensory neuropathies (HMSN); hereditary sensory neuropathies (HSNs); hereditary sensory and autonomic neuropathies; hereditary neuropathies with ulcero-mutilation; nitrofurantoin neuropathy; tomaculous neuropathy; neuropathy caused by nutritional deficiency, neuropathy caused by kidney failure and complex regional pain syndrome. Other causes include repetitive activities such as typing or working on an assembly line, medications known to cause peripheral neuropathy such as several antiretroviral drugs (ddC (zalcitabine) and ddI (didanosine), antibiotics (metronidazole, an antibiotic used for Crohn's disease, isoniazid used for tuberculosis), gold compounds (used for rheumatoid arthritis), some chemotherapy drugs (such as vincristine and others) and many others. Chemical compounds are also known to cause peripheral neuropathy including alcohol, lead, arsenic, mercury and organophosphate pesticides. Some peripheral neuropathies are associated with infectious processes (such as Guillian-Barre syndrome).

In certain embodiments, the neuropathic condition is a peripheral neuropathic condition, which is suitably pain secondary to mechanical nerve injury or painful diabetic neuropathy (PDN) or related condition.

The neuropathic condition may be acute or chronic and, in this connection, it will be understood by persons of skill in the art that the time course of a neuropathy will vary, based on its underlying cause. With trauma, the onset of symptoms may be acute, or sudden; however, the most severe symptoms may develop over time and persist for years. Inflammatory and some metabolic neuropathies have a subacute course extending over days to weeks. A chronic course over weeks to months usually indicates a toxic or metabolic neuropathy. A chronic, slowly progressive neuropathy over many years such as occurs with painful diabetic neuropathy or with most hereditary neuropathies or with a condition termed chronic inflammatory demyelinating polyradiculoneuropathy (CIDP). Neuropathic conditions with symptoms that relapse and remit include the Guillian-Barré syndrome.

In another aspect of the invention there is provided a method of treating or preventing a condition characterized by neuronal hypersensitivity in a subject comprising administering a compound of formula (I) or a pharmaceutically acceptable salt thereof.

In some embodiments, the condition characterized by neuronal hypersensitivity is a hyperalgesic condition such as fibromyalgia. In other embodiments, the condition is irritable bowel syndrome which is characterized by neuronal hypersensitivity in the gut.

In another aspect of the invention there is provided a method of treating or preventing a disorder associated with aberrant nerve regeneration comprising administering a compound of formula (I) or a pharmaceutically acceptable salt thereof.

In some embodiments, the disorder associated with aberrant nerve regeneration also includes neuronal hypersensitivity. Examples of disorders associated with aberrant nerve regeneration are breast pain, interstitial cystitis and vulvodynia. In other embodiments, the disorder is a cancer chemotherapy-induced neuropathy.

In another aspect of the invention, there is provided a method of treating or preventing inflammatory pain in a subject comprising administering a compound of formula (I) or a pharmaceutically acceptable salt thereof.

Pain related to inflammation may be acute or chronic and can be due to a number of conditions that are characterized by inflammation including, without limitation, burns such as chemical, frictional or chemical burns, autoimmune diseases such as rheumatoid arthritis and osteoarthritis, inflammatory bowel disease such as Crohn's disease and colitis, and other inflammatory diseases such as inflammatory bowel disease, carditis, dermatitis, myositis, neuritis and collagen vascular diseases.

In a further aspect, the present invention provides a method of treating or preventing impaired nerve conduction velocity in a subject comprising administering a compound of formula (I) or a pharmaceutically acceptable salt thereof.

Impaired neuronal conduction velocity is a symptom of nerve dysfunction or damage and may be present as a symptom of a large number of diseases or disorders, particularly diseases or disorders that exhibit paresthesia as a symptom. In some embodiments, the impaired nerve conduction velocity is associated with a neuropathic condition as described above. In other embodiments, the impaired nerve conduction velocity is associated with Carpel Tunnel Syndrome, ulnar neuropathy, Guillian-Barré Syndrome, fascioscapulohumeral muscular dystrophy and spinal disc herneation.

Nerve conduction velocity is assessed by evaluating the electrical conduction of motor and sensory nerves in the body. Motor nerve conduction velocity is measured by stimulation of a peripheral nerve and measuring the time taken for the electrical impulse to be detected in the muscle associated with the nerve. The time taken is measured in milliseconds and is converted to a velocity (m/s) by taking into account the distance travelled. Sensory nerve conduction is assessed in a similar manner with stimulation of a peripheral nerve and recording at a sensory site such as a finger or paw pad.

In yet a further aspect of the invention there is provided a method of producing analgesia in a subject comprising administering a compound of formula (I) or a pharmaceutically acceptable salt thereof.

In some embodiments, the subject is a subject having a neuropathic condition, an inflammatory condition, impaired nerve conduction velocity, a condition characterized by neuronal hypersensitivity or a disorder associated with aberrant nerve regeneration. In other embodiments, the subject is a subject at risk of developing neuropathic pain, inflammatory pain, pain related to impaired nerve conduction velocity, a condition characterized by neuronal hypersensitivity or a disorder associated with aberrant nerve regeneration.

In still another aspect of the invention there is provided a method of treating or preventing a cell proliferative disorder in a subject comprising administering a compound of formula (I) or a pharmaceutically acceptable salt thereof.

In some embodiments, the cell proliferative disorder is a cancer, especially where the cancer is selected from leukaemia, melanoma, prostate cancer, breast cancer, ovarian cancer, basal cell carcinoma, squamous cell carcinoma, sarquoides, fibrosarcoma, colon cancer, lung cancer and other solid tumour cancers.

In other embodiments, the cell proliferative disorder is a non-cancerous proliferative disorder. Examples of such non-cancerous proliferative disorders include dermatological disorders such as warts, keloids, psoriasis, proud flesh disorder and also the reduction in scar tissue and cosmetic remodelling.

In a further aspect the present invention provides a method of treating or preventing a disorder associated with an imbalance between bone resorption and bone formation in a subject comprising administering a compound of formula (I) or a pharmaceutically acceptable salt thereof.

In some embodiments, the disorder associated with an imbalance between bone resorption and bone formation is osteoporosis.

The subjects, individuals or patients to be treated are mammalian subjects including but not limited to humans, primates, livestock animals such as sheep, cattle, pigs, horses, donkeys and goats; laboratory test animals such as mice, rats, rabbits and guinea pigs; companion animals such as cats and dogs or captive wild animals such as those kept in zoos. In a particular embodiment, the subject is a human.

An "effective amount" means an amount necessary at least partly to attain the desired response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials. An effective amount in relation to a human patient, for example, may lie in the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage. Dosage regimes may be adjusted to provide the optimum therapeutic response. For example, several divided doses may be administered daily, weekly, monthly or other suitable time intervals, or the dose may be proportionally reduced as indicated by the exigencies of the situation.

Reference herein to "treatment" and "prevention" is to be considered in its broadest context. The term "treatment" does not necessarily imply that a subject is treated until total recovery. "Treatment" may also reduce the severity of an existing condition. The term "prevention" does not necessarily mean that the subject will not eventually contract a disease condition. The term "prevention" may be considered to include delaying the onset of a particular condition. Accordingly, treatment and prevention include alleviation of the symptoms of a particular condition or preventing or otherwise reducing the risk of developing a particular condition.

In some embodiments, the compounds of formula (I) or their pharmaceutically acceptable salts thereof may be administered together with another therapy. Administration may be in a single composition or in separate compositions simultaneously or sequentially such that both compounds or therapies are active at the same time in the body.

In some embodiments, the compounds of formula (I) or their pharmaceutically acceptable salts are administered together with another therapy to treat neuropathic or inflammatory pain or the underlying condition that is causing the neuropathic or inflammatory pain or another therapy to treat conditions characterized by neuronal hypersensitivity, disorders associated with aberrant nerve regeneration, proliferative disorders or disorders associated with an imbalance between bone resorption and bone formation. In some embodiments, the amount of the second drug may be reduced when administration is together with a compound of formula (I) or a pharmaceutically acceptable salt thereof.

Suitable additional drugs to treat pain include opiates such as morphine, codeine, dihydrocodeine, hydrocodone, acetyldihydrocodeine, oxycodone, oxymorphone and buprenorphine, and non-steroidal anti-inflammatory drugs (NSAIDs) such as aspirin, ibuprofen, naproxen, acetaminophen, diflunisal, salsalate, phenacetin, fenoprofen, ketoprofen, flurbiprofen, oxaprozin, loxoprofen, indomethacin, sulindac, etodolac, ketorolac, diclofenac, nabumetone, mefenamic acid, meclofenamic acid, flufenamic acid, tolfenamic acid, celecoxib, parecoxib, lumaricoxib, etoricoxib, firocoxib, rimesulide and licofelone.

Examples of drugs to treat neuropathies include duloxetine, pregabalin, gabapentin, phenytoin, carbamazebine, levocarnitine, tricyclic antidepressants such as amitryptiline and sodium channel blockers such as lidocaine.

Examples of chemotherapy drugs for proliferative disorders include cisplatin, carboplatin, camptothecin, carmustine, cyclophosphamide, dactinomycin, daunorubicin, dexamethasone, docetaxel, doxorubicin, etoposide, epirubicin, everolimus, gemcitibine, goserelin, trastuzumab (Herceptin®), idarubicin, interferon-alfa, irinotecan, methotrexate, mitomycin, oxaliplatin, paclitaxel, raloxifene, streptozocin, tamoxifen, topotecan, vinblastine, vincristine, abiraterone, fluorouracil, denosumab, imatinib, geftinib, lapatinib, pazopanib, rituximab, sunitinib, erlotinib and vorinistat.

Examples of drugs to treat disorders associated with an imbalance between bone formation and bone resorption include bisphosphonates such as sodium alendronate, risedronate and ibandronate, raloxifene, calcitonin, teriparatide, strontium ranelate or calcium supplements.

Examples of drugs used to treat conditions characterized by neuronal hypersensitivity, such as irritable bowel syndrome, include $5HT_3$ receptor antagonists such as alosetron (Lotronex®).

The $AT_2$ receptor antagonists of the invention are also useful in combination with radiotherapy in cancer patients.

Compositions of the Invention

While it is possible that, for use in therapy, a compound of the invention may be administered as a neat chemical, it is preferable to present the active ingredient as a pharmaceutical composition.

Thus, in a further aspect of the invention, there is provided a pharmaceutical composition comprising a compound of formula (I) or a pharmaceutically acceptable salt thereof and at least one pharmaceutically acceptable carrier.

The carrier(s) must be "acceptable" in the sense of being compatible with the other ingredients of the composition and not deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation. The compounds of the invention, together with a conventional adjuvant, carrier, excipient, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to two hundred (200) milligrams, per tablet, are accordingly suitable representative unit dosage forms. The compounds of the present invention can be administered in a wide variety of oral and parenteral dosage forms. It will be obvious to those skilled in the art that the following dosage forms may comprise, as the active component, either a compound of the invention or a pharmaceutically acceptable salt or derivative of the compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules.

A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension.

In the case of a spray, this may be achieved for example by means of a metering atomizing spray pump. To improve nasal delivery and retention the compounds according to the invention may be encapsulated with cyclodextrins, or formulated with their agents expected to enhance delivery and retention in the nasal mucosa.

Administration to the respiratory tract may also be achieved by means of an aerosol formulation in which the active ingredient is provided in a pressurized pack with a suitable propellant such as a chlorofluorocarbon (CFC) for example, dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 1 to 10 microns or less. Such a particle size may be obtained by means known in the art, for example by micronization.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The pharmaceutical compositions may comprise further active ingredients such as other therapies to treat neuropathic or inflammatory pain or the underlying condition that is causing the neuropathic or inflammatory pain or therapies to treat conditions characterized by neuronal hypersensitivity, disorders associated with aberrant nerve regeneration, proliferative disorders or disorders associated with an imbalance between bone resorption and bone formation.

The invention will now be described with reference to the following Examples which illustrate some preferred aspects of the present invention. However, it is to be understood that the particularity of the following description of the invention is not to supersede the generality of the preceding description of the invention.

Preferred Embodiments

Embodiment 1: A compound of formula (I):

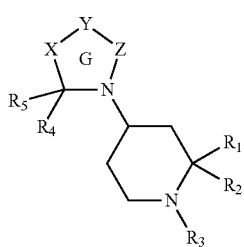

(I)

wherein Ring G is a 5 to 8 membered ring and

X is absent or is selected from —$(CR_6R_7)_n$—, —W—, —$(CR_6R_7)_m$—W—, —W—$(CR_6R_7)_m$— and —$(CR_6R_7)_p$—W—$(CR_6R_7)_p$—;

Y is —$CR_8CR_9$— wherein $R_8$ and $R_9$ together with the carbon atoms to which they are attached form an optionally substituted aromatic or heteroaromatic ring or ring system;

Z is absent or is selected from —$CR_4R_5$—, —$CR_6R_7CR_4R_5$—, —W—$CR_4R_5$—;

W is selected from —O—, —S—, —S(O)—, —$S(O)_2$—, —C(O)—, —$NR_{10}$—, —$C(O)N(R_{11})$—, —$N(R_{11})C(O)$—, —C(O)O—, —OC(O)—, —$S(O)_2N(R_{11})$—, —$N(R_{11})S(O)_2$—, —$N(R_{11})C(O)N(R_{11})$— and —$N(R_{11})S(O)_2N(R_{11})$—;

$R_1$ is selected from —$CO_2H$, —$CH_2CO_2H$, —C(O)C(O)OH, —$CH_2OH$, —$C(O)NH_2$, —CN, —$CH_2C(O)NH_2$, —$CH_2CN$, a carboxylic acid bioisostere and —$CH_2$carboxylic acid bioisostere;

$R_2$ is selected from hydrogen, alkyl, alkenyl, alkynyl, —$C_{1-6}$alkyleneR$_{12}$, —$C_{2-6}$alkenyleneR$_{12}$ and —$C_{2-6}$alkynyleneR$_{12}$;

$R_3$ is selected from —C(O)CH(aryl)(aryl) and —C(O)N(aryl)(aryl);

Each $R_4$ and $R_5$ are independently selected from hydrogen, alkyl, alkenyl, alkynyl, —$OC(R_{14})_3$, —CN, —$NO_2$, —$N(R_{13})_2$, —$CO_2R_{13}$, —$C(O)R_{13}$, —$C(O)N(R_{13})_2$, —$S(O)_2R_{13}$, —$S(O)_2N(R_{13})_2$, —$C(R_{14})_3$, cycloalkyl, cycloalkenyl, aryl, heterocyclyl and heteroaryl, or $R_4$ and $R_5$ taken together form a carbonyl group;

$R_6$ and $R_7$ are independently selected from hydrogen, alkyl, alkenyl, alkynyl, —$OR_{13}$, —$SR_{13}$, halo, —CN, —$NO_2$, —$N(R_{13})_2$, —$CO_2R_{13}$, —$C(O)R_{13}$, —$C(O)N(R_{13})_2$, —$S(O)_2R_{13}$, $S(O)_2N(R_{13})_2$, —$C(R_{14})_3$, —$OC(R_{14})_3$, cycloalkyl, cycloalkenyl, aryl, heterocyclyl and heteroaryl, or $R_6$ and $R_7$ taken together form a carbonyl group;

$R_{10}$ is selected from hydrogen, alkyl, alkenyl, alkynyl, cycloalkyl, cycloalkenyl, aryl, heterocyclyl, heteroaryl, —$C(R_{14})_3$, —$C(O)R_{13}$, —$C(O)N(R_{13})_2$, —$S(O)R_{13}$, —$S(O)_2R_{13}$, —$S(O)_2N(R_{13})_2$ and —$CO_2R_{13}$;

$R_{11}$ is selected from hydrogen and alkyl;

$R_{12}$ is selected from cycloalkyl, cycloalkenyl, aryl, heterocyclyl and heteroaryl;

Each $R_{13}$ is independently selected from hydrogen, alkyl, alkenyl, alkynyl, cycloalkyl, cycloalkenyl, aryl, heterocyclyl and heteroaryl;

Each $R_{14}$ is independently selected from hydrogen and halo;

n is selected from an integer from 1 to 4;
m is selected from an integer from 1 to 3;
p is selected from an integer of 1 or 2;

wherein each alkyl, alkenyl, alkynyl, cycloalkyl, cycloalkenyl, aryl, heterocyclyl and heteroaryl may be optionally substituted; or a pharmaceutically acceptable salt thereof.

Embodiment 2: A compound according to embodiment 1 wherein X is absent or is selected from —$(CR_6R_7)_n$—, —W—, —$(CR_6R_7)_m$—W— and —$(CR_6R_7)_p$—W—$(CR_6R_7)_p$—.

Embodiment 3: A compound according to embodiment 1 or embodiment 2 wherein Y is selected from —$CR_8CR_9$— wherein $R_8$ and $R_9$ together with the carbon atoms to which they are attached form a five or six membered monocyclic or eight to ten membered bicyclic aromatic or heteroaromatic ring selected from phenyl, pyridinyl, thiophenyl, pyrrolyl, pyrazolyl, imidazolyl, triazolyl, isoxazolyl, thiazolyl, isothiazolyl, pyridazinyl, pyrimidinyl, pyrazinyl, triazinyl, indanyl, indenyl, coumarinyl, benzofuranyl, benzothiophenyl, indolinyl, indolyl, isoindolyl, benzimidazolyl, benzo-1,3-dioxalanyl, benzo-1,4-dioxanyl, benzodithiolyl, benzodihydrodithiolyl, benzodithianyl, cyclopentyl [b]pyridinyl, indazolyl, benzoxazolyl, benzothiazolyl, naphthalenyl, tetrahydronaphthalenyl, benzopyranyl, quinolinyl, isoquinolinyl, quinazolinyl, cinnolinyl, quinoxalinyl, naphthyridinyl, phthalazinyl, benzoxazinyl, benzoxadiazinyl and pteridinyl, each of which may be optionally substituted.

Embodiment 4: A compound according to any one of embodiments 1 to 3 wherein Z is absent or is selected from —$CR_4R_5$— and —$CR_6R_7CR_4R_5$—.

Embodiment 5: A compound according to embodiment 4 wherein W is selected from —O—, —C(O)—, —$S(O)_2$—, —$N(R_{10})$—, —$C(O)N(R_{11})$—, —$N(R_{11})C(O)$—, —$S(O)_2N(R_{11})$— and —$N(R_{11})S(O)_2$—.

Embodiment 6: A compound according to embodiment 5 wherein W is —O— or —$NR_{10}$—.

Embodiment 7: A compound according to any one of embodiments 1 to 6 wherein $R_1$ is selected from —$CO_2H$, —$CH_2CO_2H$, —C(O)C(O)OH, —$C(O)NH_2$, —CN, —$C(O)NHSO_2C_{1-6}$alkyl, —$C(O)NHSO_2C_{3-8}$cycloalkyl, —$C(O)NHSO_2$phenyl, —$C(O)NHSO_2N(C_{1-6}$alkyl)$_2$, —$C(O)NHSO_2N(C_{3-8}$cycloalkyl)$_2$, —$C(O)NHSO_2N(C_{1-6}$alkyl)($C_{3-8}$cycloalkyl), —$C(O)NHSO_2CF_3$, tetrazole and tetrazolate.

Embodiment 8: A compound according to any one of embodiments 1 to 7 wherein $R_2$ is selected from hydrogen, —$C_{1-6}$alkyl, —$C_{1-4}$alkyleneR$_{12}$, —$C_{2-4}$alkenyleneR$_{12}$ and —$C_{2-4}$alkynyleneR$_{12}$.

Embodiment 9: A compound according to any one of embodiments 1 to 8 wherein $R_3$ is selected from —C(O)CH(phenyl)(phenyl) and —C(O)N(phenyl)(phenyl).

Embodiment 10: A compound according to any one of embodiments 1 to 9 wherein each $R_4$ and $R_5$ are independently selected from hydrogen —$C_{1-6}$alkyl, —$C_{2-6}$alkenyl, —$C_{2-6}$alkynyl, halo, —OH, —$OC_{1-6}$alkyl, —$OC_{2-6}$alkenyl, —$OC_{2-6}$alkynyl, —$CF_3$, —$CHF_2$, —$CH_2F$, —$OCF_3$, —$OCHF_2$, —$OCH_2F$, —CN, —$NO_2$, —$NH_2$, —$NH(C_{1-6}$alkyl), —$N(C_{1-6}$alkyl)$_2$, —NH(aryl), —$N(C_{1-6}$alkyl)(phenyl), —$N(phenyl)_2$, —$CO_2H$, —$CO_2C_{1-6}$alkyl, —$CO_2C_{2-6}$alkenyl, —$CO_2$phenyl, —$C(O)NH_2$, —$C(O)NHC_{1-6}$alkyl, —$C(O)N(C_{1-6}$alkyl)$_2$, —$C(O)C_{1-6}$alkyl, —$C(O)C_{2-6}$alkenyl, —$C(O)C_{2-6}$alkynyl, —S(O)$_2$C$_{1-6}$alkyl, —S(O)$_2$aryl, —S(O)$_2$NH$_2$, —S(O)$_2$NH(C$_{1-6}$alkyl) and —S(O)$_2$N(C$_{1-6}$alkyl)$_2$.

Embodiment 11: A compound according to any one of embodiments 1 to 11 wherein each of R$_6$ and R$_7$ are independently selected from hydrogen —C$_{1-6}$alkyl, —C$_{2-6}$alkenyl, —C$_{2-6}$alkynyl, halo, —OH, —OC$_{1-6}$alkyl, —OC$_{2-6}$alkenyl, —OC$_{2-6}$alkynyl, —CN, —NO$_2$, —NH$_2$, —NH(C$_{1-6}$alkyl), —N(C$_{1-6}$alkyl)$_2$, —NH(aryl), —N(C$_{1-6}$alkyl)(phenyl), —N(phenyl)$_2$, —CO$_2$H, —CO$_2$C$_{1-6}$alkyl, —CO$_2$C$_{2-6}$alkenyl, —CF$_3$, —CHF$_2$, —CH$_2$F, —OCF$_2$, —OCHF$_2$, —OCH$_2$F, —CO$_2$phenyl, —C(O)NH$_2$, —C(O)NHC$_{1-6}$alkyl, —C(O)N(C$_{1-6}$alkyl)$_2$, —C(O)C$_{1-6}$alkyl, —C(O)C$_{2-6}$alkenyl, —C(O)C$_{2-6}$alkynyl, —S(O)$_2$C$_{1-6}$alkyl, —S(O)$_2$aryl, —S(O)$_2$NH$_2$, —S(O)$_2$NH(C$_{1-6}$alkyl) and —S(O)$_2$N(C$_{1-6}$alkyl)$_2$.

Embodiment 12: A compound according to any one of embodiments 1 to 11 wherein R$_{10}$ is selected from hydrogen, C$_{1-6}$alkyl, —C(O)C$_{1-6}$alkyl, —C(O)C$_{2-6}$alkenyl, —C(O)C$_{2-6}$alkynyl, —C(O)C$_{2-6}$alkynyl, —CO$_2$H, —CO$_2$C$_{1-6}$alkyl, —CO$_2$C$_{2-6}$alkenyl, —CO$_2$C$_{2-6}$alkynyl, —C(O)NH$_2$, —C(O)NH(C$_{1-6}$alkyl), —C(O)NH(C$_{2-6}$alkenyl), —C(O)NH(C$_{2-6}$alkynyl), —C(O)N(C$_{1-6}$alkyl)$_2$, —SO$_2$C$_{1-6}$alkyl, —SO$_2$C$_{2-6}$alkenyl, —SO$_2$C$_{2-6}$alkynyl, —SO$_2$NH$_2$, —SO$_2$NH(C$_{1-6}$alkyl), —SO$_2$NH(C$_{2-6}$alkenyl), —SO$_2$NH(C$_{2-6}$alkynyl), —SO$_2$N(C$_{1-6}$alkyl)$_2$, —SO$_2$CF$_3$, —SO$_2$NHC(O)NH$_2$, —SO$_2$NHC(O)NH(C$_{1-6}$alkyl) and —SO$_2$NHC(O)N(C$_1$ 6alkyl)$_2$.

Embodiment 13: A compound according to any one of embodiments 1 to 11 wherein R$_{11}$ is selected from hydrogen or C$_{1-3}$alkyl.

Embodiment 14: A compound according to any one of embodiments 1 to 13 wherein R$_{12}$ is selected from cycloalkyl and aryl.

Embodiment 15: A compound according to any one of embodiments 1 to 14 wherein each R$_{13}$ is independently selected from hydrogen, C$_{1-6}$alkyl, C$_{3-6}$cycloalkyl, C$_{5-6}$cycloalkenyl and phenyl.

Embodiment 16: A compound according to any one of embodiments 1 to 15 wherein n is 2 or 3.

Embodiment 17: A compound according to any one of embodiments 1 to 16 wherein m is 1 or 2.

Embodiment 18: A compound according to embodiment 1 which is a compound of formula (II):

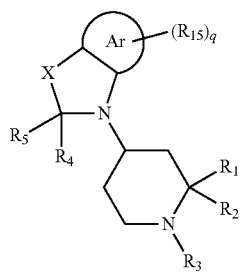

(II)

wherein

X is selected from —(CR$_6$R$_7$)$_n$—, —W—, —(CR$_6$R$_7$)$_m$—W—, —W—(CR$_6$R$_7$)$_m$— and —(CR$_6$R$_7$)$_p$—W—(CR$_6$R$_7$)$_p$—;

Ar is an aromatic or heteroaromatic ring or ring system;

R$_1$ is selected from —CO$_2$H, —CH$_2$CO$_2$H, —C(O)C(O)OH, —CH$_2$OH, —C(O)NH$_2$, —CN, —CH$_2$C(O)NH$_2$, —CH$_2$CN, a carboxylic acid bioisostere and —CH$_2$carboxylic acid bioisostere;

R$_2$ is selected from hydrogen, alkyl, alkenyl, alkynyl, —C$_{1-6}$alkyleneR$_{12}$, —C$_{2-6}$alkenyleneR$_{12}$ and —C$_{2-6}$alkynyleneR$_{12}$;

R$_3$ is selected from —C(O)CH(aryl)(aryl) and —C(O)N(aryl)(aryl);

Each R$_4$ and R$_5$ are independently selected from hydrogen, alkyl, alkenyl, alkynyl, —OC(R$_{14}$)$_3$, —CN, —NO$_2$, —N(R$_{13}$)$_2$, —CO$_2$R$_{13}$, —C(O)R$_{13}$, —C(O)N(R$_{13}$)$_2$, —S(O)$_2$ R$_{13}$, —S(O)$_2$N(R$_{13}$)$_2$, —C(R$_{14}$)$_3$, cycloalkyl, cycloalkenyl, aryl, heterocyclyl and heteroaryl, or R$_4$ and R$_5$ taken together from a carbonyl group;

R$_6$ and R$_7$ are independently selected from hydrogen, alkyl, alkenyl, alkynyl, —OR$_{13}$, —SR$_{13}$, halo, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl, or R$_6$ and R$_7$ taken together form a carbonyl group;

W is selected from —O—, —S—, —S(O)—, —S(O)$_2$—, —C(O)—, —NR$_{10}$—, —C(O)N(R$_{11}$)—, —N(R$_{11}$)C(O)—, —C(O)O—, —OC(O)—, —S(O)$_2$N(R$_{11}$)—, —N(R$_{11}$)S(O)$_2$—, —N(R$_{11}$)C(O)N(R$_{11}$)— and —N(R$_{11}$)S(O)$_2$N(R$_{11}$)—;

R$_{10}$ is selected from hydrogen, alkyl, alkenyl, alkynyl, cycloalkyl, cycloalkenyl, aryl, heterocyclyl, heteroaryl, —C(R$_{14}$)$_3$, —C(O)R$_{13}$, —C(O)N(R$_{13}$)$_2$, —S(O)R$_{13}$, —S(O)$_2$R$_{13}$, —S(O)$_2$N(R$_{13}$)$_2$ and —CO$_2$R$_{13}$;

R$_{11}$ is selected from hydrogen and alkyl;

R$_{12}$ is selected from cycloalkyl, cycloalkenyl, aryl, heterocyclyl and heteroaryl;

Each R$_{13}$ is independently selected from hydrogen, alkyl, alkenyl, alkynyl, cycloalkyl, cycloalkenyl, aryl, heterocyclyl and heteroaryl;

Each R$_{14}$ is independently selected from hydrogen and halo;

Each R$_{15}$ is independently selected from —C$_{1-6}$alkyl, —C$_{2-6}$alkenyl, —C$_{2-6}$alkynyl, —OR$_{13}$, —SR$_{13}$, halo, —CN, —NO$_2$, —N(R$_{13}$)$_2$, —CO$_2$R$_{13}$, —CON(R$_{13}$)$_2$, —C(O)R$_{13}$, —S(O)$_2$R$_{13}$, —S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl;

m is selected from an integer from 1 to 3;

n is selected from an integer from 1 to 4;

p is selected from an integer of 1 or 2; and q is 0 or an integer of 1 to 4;

wherein each alkyl, alkenyl, alkynyl, cycloalkyl, cycloalkenyl, aryl, heterocyclyl and heteroaryl may be optionally substituted; or a pharmaceutically acceptable salt thereof.

Embodiment 19: A pharmaceutical composition comprising a compound of formula (I) according to any one of embodiments 1 to 18 or a pharmaceutically acceptable salt thereof and a pharmaceutically acceptable carrier.

Embodiment 20: A method of treating or preventing neuropathic pain in a subject comprising administering a compound of formula (I) according to any one of embodiments 1 to 18 or a pharmaceutically acceptable salt thereof.

Embodiment 21: A method of treating or preventing a condition characterized by neuronal hypersensitivity in a subject comprising administering a compound of formula (I) according to any one of embodiments 1 to 18 or a pharmaceutically acceptable salt thereof.

Embodiment 22: A method of treating or preventing inflammatory pain in a subject comprising administering a compound of formula (I) according to any one of embodiments 1 to 18 or a pharmaceutically acceptable salt thereof.

Embodiment 23: A method of treating or preventing impaired nerve conduction velocity in a subject comprising administering a compound of formula (I) according to any one of embodiments 1 to 18 or a pharmaceutically acceptable salt thereof.

Embodiment 24: A method of producing analgesia in a subject comprising administering a compound of formula (I) according to any one of embodiments 1 to 18 or a pharmaceutically acceptable salt thereof.

Embodiment 27: A method of treating or preventing a cell proliferative disorder in a subject comprising administering a compound of formula (I) according to any one of embodiments 1 to 18 or a pharmaceutically acceptable salt thereof.

Embodiment 28: A method of treating or preventing a disorder associated with an imbalance between bone resorption and bone formation in a subject comprising administering a compound of formula (I) according to any one of embodiments 1 to 18 or a pharmaceutically acceptable salt thereof.

Embodiment 29: A method of treating a disorder associated with aberrant nerve regeneration in a subject comprising administering a compound of formula (I) according to any one of embodiments 1 to 18 or a pharmaceutically acceptable salt thereof.

EXAMPLES

Abbreviations aq: aqueous; DCE: 1,2-dichloroethane; DCM: dichloromethane; DIBAL-H: diisobutylaluminium hydride; DIPEA: diisopropylethylamine; DMP: Dess Martin Periodinane; EtOAc: ethyl acetate; (ES$^+$): electrospray ionization, positive mode; h: hours; HCl: hydrochloric acid; HPLC: high performance liquid chromatography; i-PrOH: isopropanol; LCMS: liquid chromatography-mass spectrometry; LiOH: lithium hydroxide; M: molar; [M+H]$^+$: protonated molecular ion; MeCN: acetonitrile; MeOH: methanol; min: minutes; MS: mass spectrometry; m/z: mass-to-charge ratio; NaOH: sodium hydroxide; RT: room temperature (ca. 20° C.); R$_t$: retention time; sat: saturated; SCX: strong cation exchange; THF: tetrahydrofuran; UV: ultra-violet General Experimental Conditions All starting materials and solvents were obtained either from commercial sources or prepared according to literature procedure.

Silica gel chromatography was performed on an automated flash chromatography system, such as CombiFlash Companion or CombiFlash Rf system, using RediSep® Rf pre-packed silica (230-400 mesh, 40-63 μm) cartridges.

Analytical LCMS experiments to determine retention times and associated mass ions were performed using an Agilent 1200 series HPLC system coupled to an Agilent 6110 or 6120 series single quadrupole mass spectrometer running one of the analytical methods described below.

Preparative HPLC purifications were performed using a Waters X-Select CSH C18, 5 μm, 19×50 mm column using a gradient of 0.1% formic acid in MeCN and 0.1% aqueous formic acid. Fractions were collected following detection by either UV at a single wavelength measured by a variable wavelength detector on a Gilson 215 or a Varian PrepStar preparative HPLC, or by mass ion and UV detection at a single wavelength measured by a ZQ single quadropole mass spectrometer, with positive and negative ion electrospray, and dual wavelength detection on a Waters FractionLynx LCMS.

SCX resin was purchased from Sigma Aldrich or Silicycle and washed with MeOH prior to use.

Analytical Methods

Method 1—Acidic 4 Min Method

Column: Waters X-Select CSH C18, 2.5 μm, 4.6×30 mm

Detection: UV at 254 nm (or 215 nm), MS ionization method-electrospray

Solvent A: Water/0.1% Formic acid

Solvent B: MeCN/0.1% Formic acid

Gradient:

| Time | % A | % B | Flow rate (mL/min) |
|---|---|---|---|
| 0.0 | 95 | 5 | 2.5 |
| 3.0 | 5 | 95 | 2.5 |
| 3.01 | 5 | 95 | 4.5 |
| 3.5 | 5 | 95 | 4.5 |
| 3.6 | 95 | 5 | 3.5 |
| 4.0 | 95 | 5 | 2.5 |

Method 2—Acidic 15 Min Method

Column: Waters X-Select CSH C18, 2.5 μm, 4.6×30 mm

Detection: UV at 254 nm (or 215 nm), MS ionization method-electrospray

Solvent A: Water/0.1% Formic acid

Solvent B: MeCN/0.1% Formic acid

Gradient:

| Time | % A | % B | Flow rate (mL/min) |
|---|---|---|---|
| 0.0 | 95.0 | 5.0 | 2.5 |
| 14.0 | 5.0 | 95.0 | 2.5 |
| 14.01 | 5.0 | 95.0 | 4.5 |
| 14.50 | 5.0 | 95.0 | 4.5 |
| 14.60 | 95.0 | 5.0 | 3.5 |
| 15.00 | 95.0 | 5.0 | 2.5 |

Example 1

Compound 1 (2S,4R)-4-(7,8-Difluoro-3,4-dihydrobenzo[b][1,4]oxazepin-5 (2H)-yl)-1-(2,2-diphenylacetyl)piperidine-2-carboxylic acid

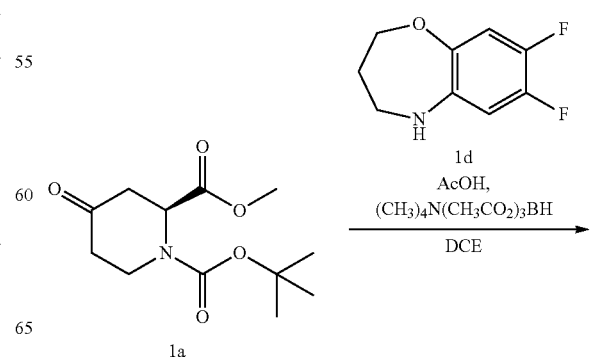

-continued

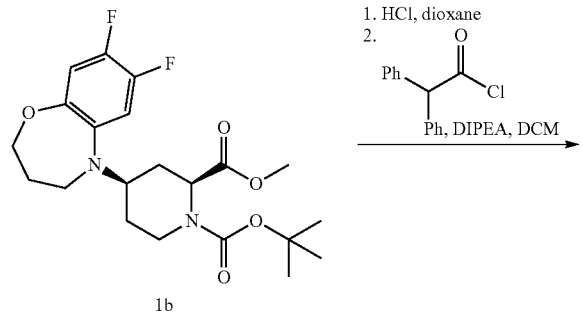
1b

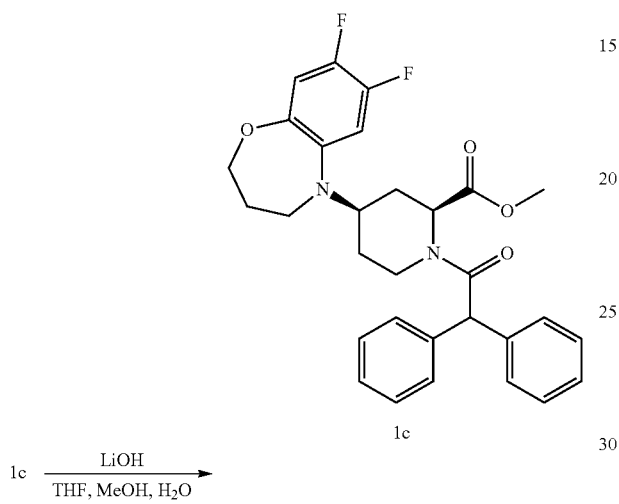
1c

1c → (LiOH, THF, MeOH, H₂O)

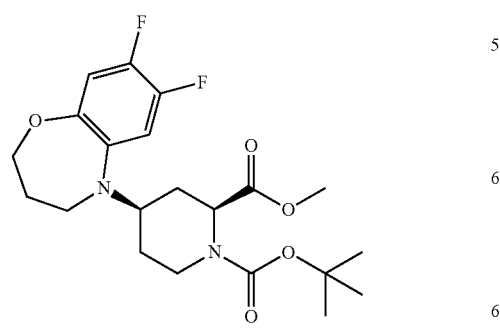
1

Procedure for the preparation of 1b

A solution of (S)-1-tert-butyl 2-methyl 4-oxopiperidine-1,2-dicarboxylate (290 mg, 1.13 mmol) in AcOH (2 mL) was treated with a solution of 7,8-difluoro-2,3,4,5-tetrahydrobenzo [b][1,4]oxazepine (150 mg, 0.81 mmol) in DCE (2 mL), followed by Ti(ⁱPrO)₄ (0.24 mL, 0.81 mmol) and then sodium triacetoxyborohydride (275 mg, 1.30 mmol) in three portions over 15 min. The reaction mixture was stirred at RT for 64 h. After this time, the mixture was concentrated in vacuo onto silica gel and the product was purified by silica gel chromatography (0-40% EtOAc in isohexane) to afford (2S,4R)-1-tert-butyl 2-methyl 4-(7, 8-difluoro-3,4-dihydrobenzo[b][1,4]oxazepin-5 (2H)-yl)piperidine-1,2-dicarboxylate 1b (150 mg, 42%) as a colourless gum: m/z 427 [M+H]⁺ (ES⁺) at $R_t$ 2.67 min (Method 1).

Procedure for the preparation of 1c

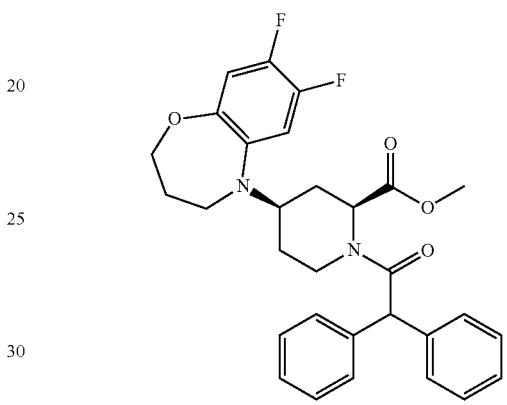

A solution of (2S,4R)-1-tert-butyl 2-methyl 4-(7,8-difluoro-3,4-dihydrobenzo[b][1,4]oxazepin-5(2H)-yl)piperidine-1,2-dicarboxylate 1b (155 mg, 0.363 mmol) in DCM (1 mL) was treated with 4M HCl in dioxane (1.4 mL, 5.6 mmol). The mixture was stirred at RT for 3 h and then concentrated in vacuo. The resulting solid was dissolved in DCM (2 mL) and the solution was cooled with iced water and treated with DIPEA (250 μL, 1.4 mmol) followed by 2,2-diphenylacetyl chloride (99 mg, 0.43 mmol). The mixture was warmed to RT, stirred for 1.5 h and then concentrated in vacuo. The product was purified by silica gel chromatography (0-45% EtOAc in isohexane) to afford (2S,4R)-methyl 4-(7,8-difluoro-3,4-dihydrobenzo[b][1,4]oxazepin-5(2H)-yl)-1-(2,2-diphenylacetyl)piperidine-2-carboxylate 1c (170 mg, 75%) as a white solid: m/z 521 [M+H]⁺ (ES⁺) at $R_t$ 2.78 min (Method 1).

Procedure for the preparation of 1

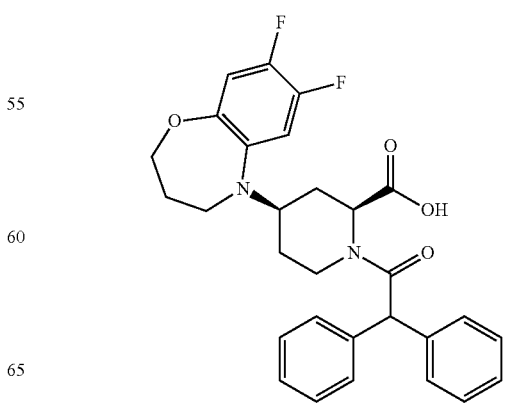

A mixture of (2S,4R)-methyl 4-(7,8-difluoro-3,4-dihydrobenzo[b][1,4]oxazepin-5(2H)-yl)-1-(2,2-diphenylacetyl)piperidine-2-carboxylate 1c (170 mg, 0.33 mmol) and LiOH (12 mg, 0.49 mmol) in THF (2 mL), MeOH (0.5 mL) and water (0.5 mL) was stirred at RT for 18 h. The mixture was acidified with 1M HCl and then concentrated in vacuo. The residue was partitioned between DCM (5 mL) and water (5 mL) and the mixture was passed through a hydrophobic frit. The organic solution was concentrated in vacuo and the product was purified by silica gel chromatography (0-50% (1% AcOH in EtOAc) in isohexane) to afford (2S,4R)-4-(7, 8-difluoro-3,4-dihydrobenzo[b][1,4]oxazepin-5(2H)-yl)-1-(2,2-diphenylacetyl)piperidine-2-carboxylic acid 1 (123 mg, 74%) as a white solid: m/z 507 [M+H]$^+$ (ES$^+$), 505 [M−H]$^−$ (ES$^−$) at R$_t$ 7.49 min (Method 2).

Procedure for the preparation of 1d

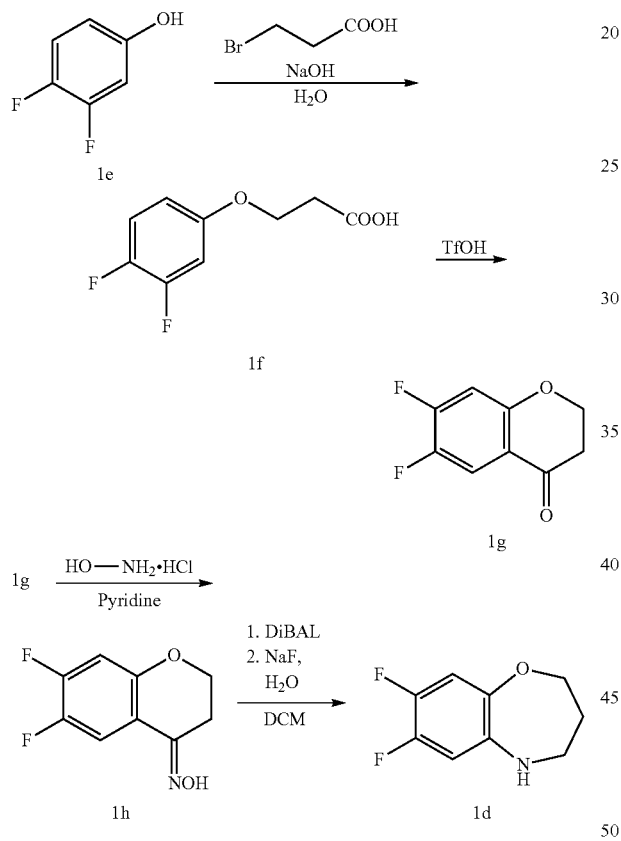

Step 1: A mixture of 3,4-difluorophenol 1e (5.0 g, 38 mmol), 3-bromopropanoic acid (6.5 g, 42 mmol) and NaOH (3.1 g, 77 mmol) in water (50 mL) was refluxed for 4.5 h. After cooling to RT, the pH of the reaction mixture was adjusted to ~2 by the addition of 3M HCl and the product was extracted with EtOAc (200 mL). The organic solution was washed with sat. brine, dried over MgSO$_4$ and filtered. The solution was concentrated in vacuo and the residue was purified by silica gel chromatography (0-60% EtOAc in isohexane) to afford 3-(3,4-difluorophenoxy)propanoic acid 1f (1.9 g, 22%) as a cream solid: m/z 201 [M−H]$^−$ (ES$^−$) at R$_t$ 1.71 min (Method 1).

Step 2: A mixture of 3-(3,4-difluorophenoxy)propanoic acid 1f (0.50 g, 2.5 mmol) and triflic acid (5.0 mL, 56 mmol) was stirred at RT for 18 h. After this time, the reaction mixture was poured in to iced water (30 mL). The resultant solid was collected by filtration to yield 6,7-difluorochroman-4-one 1g (370 mg, 81%) as a white solid: m/z 185 [M+H]$^+$ (ES$^+$) at R$_t$ 1.76 min (Method 1).

Step 3: Hydroxylamine hydrochloride (0.3 g, 4 mmol) was added to a stirred solution 6,7-difluorochroman-4-one 1g (0.4 g, 2 mmol) in pyridine (4 mL). The mixture was stirred at RT for 20 h and then concentrated in vacuo. The residue was partitioned between EtOAc (25 mL) and water (30 mL). The aqueous layer was reextracted with EtOAc (25 mL) then the combined organic layers were washed with sat. brine (25 mL), dried over MgSO$_4$ and filtered. The solution was concentrated in vacuo and the residue was purified by silica gel chromatography (12 g, 0-50% EtOAc in isohexane) to afford 6,7-difluorochroman-4-one oxime 1h (275 mg, 69%) as a white solid: m/z 200 [M+H]$^+$ (ES$^+$) at R$_t$ 1.85 min (Method 1).

Step 4: DIBAL-H (1M in hexane, 8.1 mL, 8.1 mmol) was added portionwise to a stirred solution of 6,7-difluorochroman-4-one oxime 1h (270 mg, 21.4 mmol) in DCM (12 mL) over 10 min under an atmosphere of nitrogen and whilst chilling with iced water. After 5 min the solution was warmed to RT and stirred for 5 h. The mixture was cooled with iced water and powdered NaF (2 g) was added, followed by water (1 mL) cautiously. The suspension was stirred for 30 min then filtered through celite which was then washed with EtOAc. The filtrate was concentrated in vacuo and the residue was purified by silica gel chromatography (12 g, 0-50% EtOAc in isohexane) to afford 7,8-difluoro-2, 3,4,5-tetrahydrobenzo[b][1,4]oxazepine 1d (170 mg, 66%) as a white solid: m/z 186 [M+H]$^+$ (ES$^+$) at R$_t$ 1.56 min (Method 1).

Example 2

Compound 2 (2S,4R)-1-(2,2-Diphenylacetyl)-4-(8-fluoro-3,4 dihydrobenzo[b][1,4]oxazepin-5(2H)-yl) piperidine-2-carboxylic acid

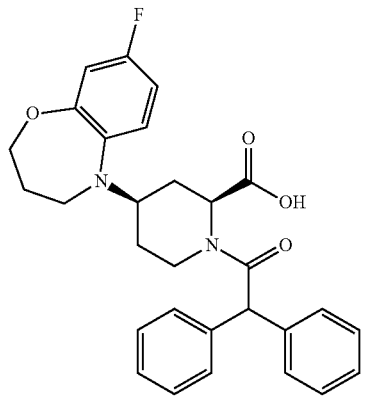 [SMILES: O=C(O)[C@@H]1C[C@H](N2CCCOc3cc(F)ccc32)CCN1C(=O)C(c1ccccc1)c1ccccc1]

(2S,4R)-1-(2,2-Diphenylacetyl)-4-(8-fluoro-3,4 dihydrobenzo[b][1,4]oxazepin-5(2H)-yl)piperidine-2-carboxylic acid 2 (48 mg, 34% for final step) was prepared in essentially the same manner as for Compound 1 (Example 1) except that 7-fluoro-2,3,4,5-tetrahydrobenzo[b][1,4]oxazepine 2a was used instead of 7,8-difluoro-2,3,4,5-tetrahydrobenzo[b][1,4]oxazepine 1d in step 1: m/z 489 [M+H]$^+$ (ES$^+$) at R$_t$ 7.18 min (Method 2).

Procedure for the preparation of 2a

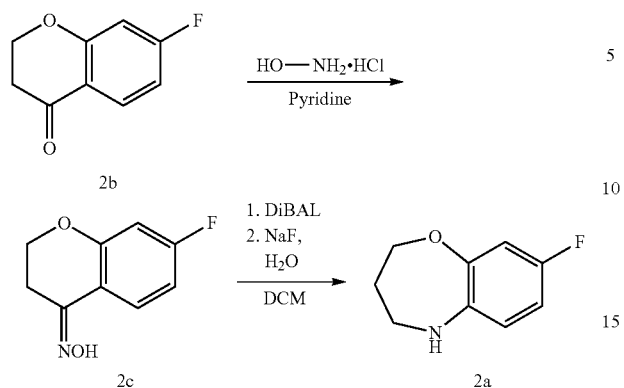

Step 1: Hydroxylamine hydrochloride (0.46 g, 6.6 mmol) was added to a stirred solution of 7-fluorochroman-4-one 2b (0.55 g, 3.3 mmol) in pyridine (5 mL). The mixture was stirred at RT for 3 h and then concentrated in vacuo. The residue was partitioned between EtOAc (25 mL) and water (30 mL). The aqueous layer was reextracted with EtOAc (25 mL) then the combined organic layers were washed with sat. brine (25 mL), dried over MgSO$_4$ and filtered. The solution was concentrated in vacuo and the residue was purified by silica gel chromatography (12 g, 0-25% EtOAc/isohexane) to afford 7-fluorochroman-4-one oxime 2c (520 mg, 86%) as an off-white solid: m/z 182 [M+H]$^+$ (ES$^+$) at R$_t$ 1.70 min (Method 1).

Step 2: DIBAL-H (1M in hexane) (17.2 mL, 17.2 mmol) was added portionwise to a stirred solution of 7-fluorochroman-4-one oxime 2c (520 mg, 2.9 mmol) in DCM (20 mL) over 15 min under an atmosphere of nitrogen and whilst chilling with iced water. After 5 min the solution was warmed to RT and stirred for 2 h. The mixture was cooled with iced water and powdered NaF (3 g) was added, followed by water (1.5 mL) cautiously. The suspension was stirred for 30 min then filtered through celite which was then washed with EtOAc. The filtrate was concentrated in vacuo and the residue was purified by silica gel chromatography (12 g, 0-15% EtOAc/isohexane) to afford 8-fluoro-2,3,4,5-tetrahydrobenzo[b][1,4]oxazepine 2a (440 mg, 90%) as a pale orange solid: m/z 168 [M+H]$^+$ (ES$^+$) at R$_t$ 0.61 min (Method 1).

Example 3

Compound 3 (2S,4R)-1-(2,2-Diphenylacetyl)-4-(7-fluoro-3,4dihydrobenzo[b][1,4]oxazepin-5(2H)-yl) piperidine-2-carboxylic acid ((2S,4R)-1-(2,2-Diphenylacetyl)-4-(7-fluoro-3,4dihydrobenzo[b][1,4]oxazepin-5(2H)-yl) piperidine-2-carboxylic acid 3 (61 mg, 94% for final step) was prepared in essentially the same manner as for Compound 1 (Example 1) except that 7-fluoro-2,3,4,5-tetrahydrobenzo[b][1,4]oxazepine (prepared in the same manner as compound 2a) was used instead of 7,8-difluoro-2,3,4,5-tetrahydrobenzo[b][1,4]oxazepine 1d in step 1: m/z 489 [M+H]$^+$ (ES$^+$) at R$_t$ 6.93 min (Method 2).

Example 4

Compound 4 (2S,4R)-4-(3,4-Dihydrobenzo[b][1,4]oxazepin-5(2H)-yl)-1-(2,2-diphenylacetyl)piperidine-2-carboxylic acid

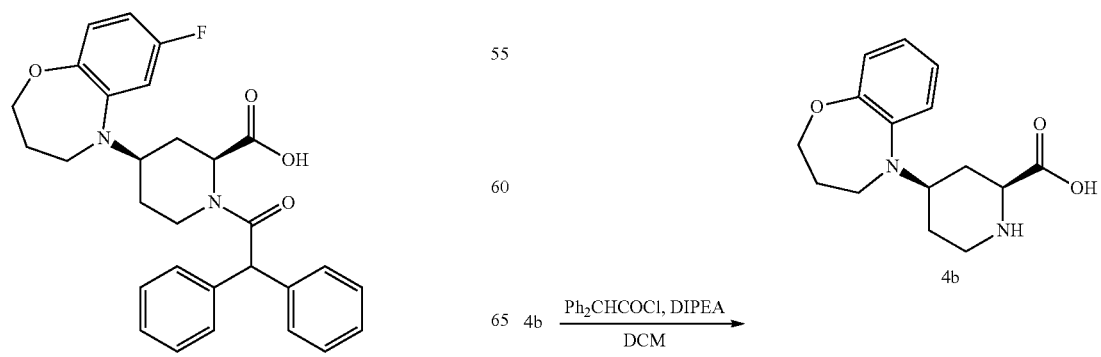

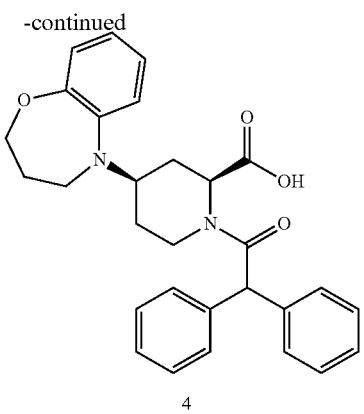

4

Procedure for the preparation of 4a

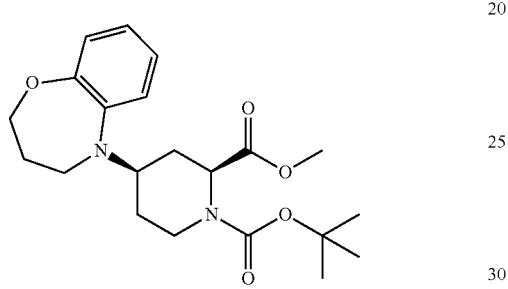

A solution of (S)-1-tert-butyl 2-methyl 4-oxopiperidine-1,2-dicarboxylate 1a (480 mg, 1.9 mmol) in AcOH (2 mL) was treated with a solution of 2,3,4,5-tetrahydrobenzo[b][1,4]oxazepine (200 mg, 1.3 mmol) in DCE (2 mL), followed by Ti($^i$PrO)$_4$ (0.39 mL, 1.3 mmol). The mixture was cooled with iced water and then sodium triacetoxyborohydride (455 mg, 2.14 mmol) was added in three portions over 20 min. The reaction mixture was warmed to RT and stirred for 20 h. After this time, the reaction mixture was concentrated in vacuo and the residue was partitioned between DCM (50 mL) and sat. NaHCO$_3$ solution (25 mL). The organic solution was washed with brine (20 mL), dried over Na$_2$SO$_4$, filtered and concentrated in vacuo. The product was purified by silica gel chromatography (0-20% EtOAc in isohexane) to (2S,4R)-1-tert-butyl 2-methyl 4-(3,4-dihydrobenzo[b][1,4]oxazepin-5(2H)-yl)piperidine-1,2-dicarboxylate 4a (350 mg, 63%) as a colourless gum: m/z 391 [M+H]$^+$ (ES$^+$) at R$_t$ 2.44 min (Method 1).

Procedure for the preparation of 4b

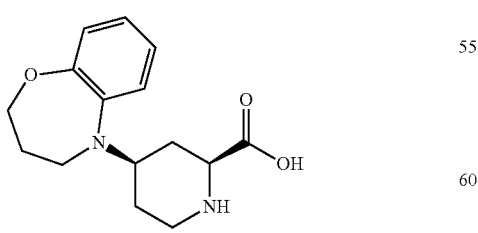

A solution of (2S,4R)-1-tert-butyl 2-methyl 4-(3,4-dihydrobenzo[b][1,4]oxazepin-5(2H)-yl) piperidine-1,2-dicarboxylate 4a (340 mg, 0.87 mmol) in 1,4-dioxane (2 mL) was treated with 4M HCl in dioxane (2.2 mL, 8.8 mmol) and the mixture was stirred at RT for 23 h. The mixture was diluted with Et$_2$O (12 mL), stirred for 20 minutes and the resultant solid collected by filtration and washed with Et$_2$O (15 mL). The solid was dissolved in THF (3 mL) and MeOH (0.75 mL) and LiOH (85 mg, 3.5 mmol) and water (0.75 mL) were added. The mixture was stirred at RT for 24 h and then acidified with 1M HCl. The mixture was concentrated in vacuo and the residue was purified by capture and release using SCX; the product was eluted with 1% NH$_3$ in MeOH. The solution was concentrated in vacuo to provide (2S,4R)-4-(3,4-dihydrobenzo[b][1,4]oxazepin-5(2H)-yl)piperidine-2-carboxylic acid 4b (192 mg, 76%) as a white solid: m/z 277 [M+H]$^+$ (ES$^+$), 275 [M–H]$^-$ (ES$^-$) at R$_t$ 0.83 min (Method 1).

Procedure for the preparation of 4

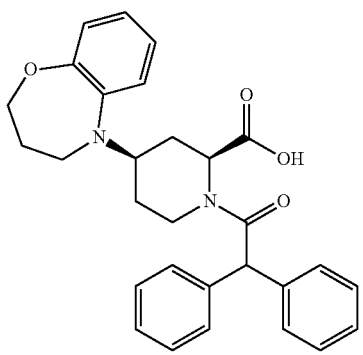 [SMILES: O=C(O)[C@@H]1C[C@H](N2CCCOc3ccccc32)CCN1C(=O)C(c1ccccc1)c1ccccc1]

DIPEA (95 µL, 0.54 mmol) was added to a stirred solution of (2S,4R)-4-(3,4-dihydrobenzo[b][1,4]oxazepin-5(2H)-yl)piperidine-2-carboxylic acid 4b (50 mg, 0.18 mmol) in DCM (1 mL). The mixture was stirred for 5 min then 2,2-diphenylacetyl chloride (46 mg, 0.18 mmol) was added. After stirring for 3 h at RT the mixture was concentrated in vacuo. The residue was partitioned between a mixture of water (6 mL) and NaOH (2M, 0.5 mL) and Et$_2$O (20 mL). The aqueous phase was acidified with 1M HCl and the product was extracted with Et$_2$O (20 mL). The organic solution was dried over MgSO$_4$, filtered and concentrated in vacuo. The product was purified by silica gel chromatography (0-60% (1% AcOH in EtOAc) in isohexane) to afford (2S,4R)-4-(3,4-dihydrobenzo[b][1,4]oxazepin-5(2H)-yl)-1-(2,2-diphenylacetyl)piperidine-2-carboxylic acid 4 (20 mg, 21%) as a white solid: m/z 471 [M+H]$^+$ (ES$^+$), 469 [M–H]$^-$ (ES$^-$) at R$_t$ 2.33 min (Method 1).

Example 5

Compound 5 (2S,4R)-1-(2,2-Diphenylacetyl)-4-(7-methoxy-2,3,4,5-tetrahydro-1H-benzo[b]azepin-1-yl)piperidine-2-carboxylic acid

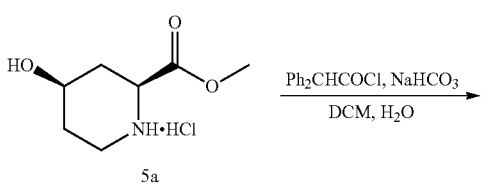

5a

53

-continued

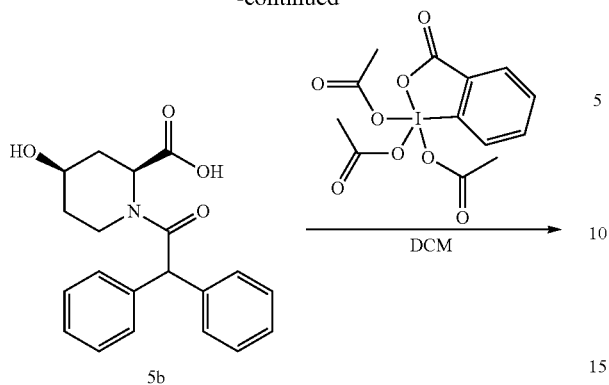

5b

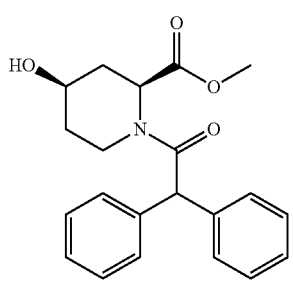 [SMILES: COC(=O)[C@@H]1C[C@H](O)CCN1C(=O)C(c1ccccc1)c1ccccc1]

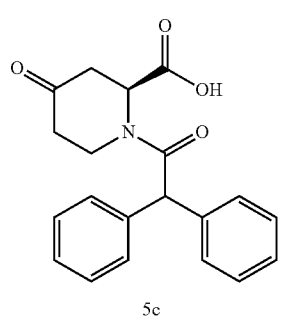

5c

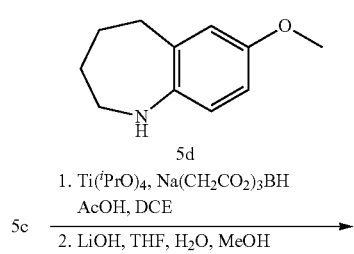

5d 5c  1. Ti($^i$PrO)$_4$, Na(CH$_2$CO$_2$)$_3$BH
       AcOH, DCE
    ───────────────────────────→
    2. LiOH, THF, H$_2$O, MeOH

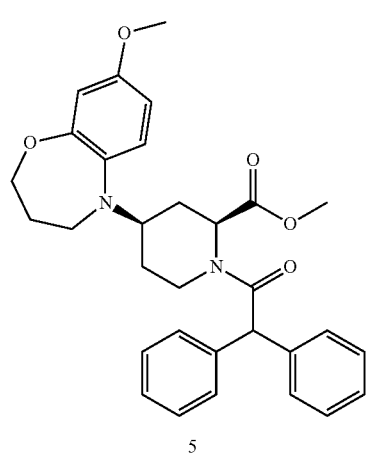

5

54

Procedure for the preparation of 5b 2,2-Diphenylacetyl chloride (680 mg, 2.9 mmol) to a biphasic mixture of (2S,4R)-methyl 4-hydroxypiperidine-2-carboxylate hydrochloride 5a (520 mg, 2.7 mmol) and NaHCO$_3$ (490 mg, 5.9 mmol) in DCM (6 mL) and water (3 mL). The mixture was stirred at RT for 20 h and then separated by passing through a hydrophobic frit. The organic solution was concentrated in vacuo and the product was purified by silica gel chromatography (0-100% isohexane in EtOAc) to afford (2S,4R)-methyl 1-(2,2-diphenylacetyl)-4-hydroxypiperidine-2-carboxylate 5b (830 mg, 87%) as a white solid: m/z 354 [M+H]$^+$ (ES$^+$) at R$_t$ 1.88 min (Method 1).

Procedure for the preparation of 5c

DMP (1.3 g, 3.0 mmol) was added to a solution of (2S,4R)-methyl 1-(2,2-diphenylacetyl)-4-hydroxypiperidine-2-carboxylate 5b (830 mg, 2.3 mmol) in anhydrous DCM (20 mL) and the mixture was stirred at RT, under nitrogen, for 70 h. Sodium thiosulfate solution (0.25 M, 20 mL) was added followed by sat. aq. NaHCO$_3$ solution, and the resulting biphasic mixture was stirred rapidly for 30 min. The layers were separated, and the organic solution was washed with sat. aq. NaHCO$_3$ and then concentrated in vacuo. The product was purified by silica gel chromatography (0-100% isohexane in EtOAc) to afford (S)-methyl 1-(2,2-diphenylacetyl)-4-oxopiperidine-2-carboxylate 5c (790 mg, 92%) as a thick colourless oil: m/z 352 [M+H]$^+$ (ES$^+$) at R$_t$ 2.01 min (Method 1).

Procedure for the preparation of 5

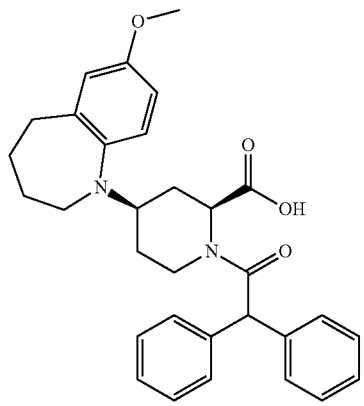 [SMILES: COc1ccc2c(c1)CCCCN2[C@@H]1CCN(C(=O)C(c2ccccc2)c2ccccc2)[C@H](C(=O)O)C1]

To a solution of (S)-methyl 1-(2,2-diphenylacetyl)-4-oxopiperidine-2-carboxylate 5c (200 mg, 0.6 mmol) in AcOH (2 mL) was added a solution of 7-methoxy-2,3,4,5-tetrahydro-1H-benzo[b]azepine 5d (72 mg, 0.41 mmol) in anhydrous DCE (2 mL), followed by Ti($^i$PrO)$_4$ (0.12 mL, 0.41 mmol). The resulting suspension was stirred at RT for 10 min, then sodium triacetoxyborohydride (140 mg, 0.65 mmol) was added and the mixture was stirred at RT for 20 h. The mixture was concentrated in vacuo onto silica gel and the product was purified by silica gel chromatography (20-40% EtOAc in isohexane) to afford a 2:1 mixture of cis and trans diastereoisomers. The mixture was dissolved in THF (1.6 mL), MeOH (0.4 mL) and water (0.4 mL) and treated with LiOH (19 mg, 0.79 mmol). The mixture was stirred at RT for 20 h and then acidified with 1 M HCl and concentrated in vacuo. The residue was partitioned between water (5 mL) and DCM (5 mL) and passed through a hydrophobic frit. The organic solution was concentrated in vacuo and the product was purified by silica gel chromatography (0-50% (1% AcOH in EtOAc) in isohexane) to afford (2S,4R)-1-(2,2-diphenylacetyl)-4-(7-methoxy-2,3,4,5-tetrahydro-1H-benzo[b]azepin-1-yl)piperidine-2-carboxylic acid 5 (24 mg, 10%) as a white solid: m/z 499 [M+H]$^+$ (ES$^+$), 497 [M−H]$^−$ (ES$^−$) at R$_t$ 5.60 min (Method 2).

Biological Example 1

AT$_2$ Receptor Binding

Materials

Reagents were purchased from Sigma-Aldrich, unless otherwise specified. Dialyzed fetal bovine serum (FBS) was from Life Technologies (cat. no. 10073772). Valiscreen® human angiotensin AT$_2$ receptor cell line (cat. no. ES-070-C), [$^{125}$I]CGP 42112A (cat. no. NEX324025UC) and MicroScint™ 40 (cat. no. 6013641) were purchased from PerkinElmer. CGP 42112A (cat. no. 2569) and PD 123,319 ditrifluoroacetate (cat. no. 1361) were from Tocris Biosciences. EMA401 [(S)-2-(diphenylacetyl)-1,2,3,4-tetrahydro-6-methoxy-5-(phenylmethoxy)-3-isoquinoline carboxylic acid] was obtained by synthesis using the method described in WO2012/010843.

Media and Solutions
1. Growth medium
   EX-CELL® CHO DHFR$^−$ medium
   10% FBS, dialysed
   1 mM sodium pyruvate
   2 mM L-glutamine
2. Harvesting buffer
   PBS
   2 mM EDTA
3. Suspension buffer
   50 mM Tris-HCl, pH 7.4
   10 mM EDTA
4. Resuspension buffer
   50 mM Tris-HCl, pH 7.4
   0.1 mM EDTA
   0.1% sucrose
5. Binding assay buffer
   50 mM Tris-HCl, pH 7.4
   5 mM MgCl$_2$
   1 mM EDTA
   0.1% gelatin
6. Wash buffer
   50 mM Tris-HCl, pH 7.4

Procedure for Membrane Preparation

Valiscreen® CHO-K1 cells stably expressing the human AT$_2$ receptor were cultured in growth medium.
Cells were seeded into T-175 flasks and grown to 70-80% confluence.
Medium was removed from confluent flasks and cells were washed with warm PBS.
Cells were harvested by incubating with harvesting buffer for 10 min at 37° C., and then transferred to a centrifuge tube on ice.
Cells were centrifuged at 200 g for 5 min at 4° C.
Cell pellets were homogenised in ice-cold suspension buffer.
Homogenates were centrifuged at 40,000 g for 15 min at 4° C.
Pellets were resuspended in ice-cold resuspension buffer and centrifuged at 40,000 g for 15 min at 4° C.
Final pellets were homogenised in ice-cold resuspension buffer.
Protein concentrations were determined by BCA assay method with BSA as standard.

Compound Preparation

Compounds were prepared from 10 mM stock solutions in 100% DMSO. Dilutions were made using electronic multi-channel pipettes. The compounds CGP 42112A (from 1 mM stock in water) and EMA401 (from 10 mM stock in 100% DMSO) were included as standards in each experiment.

Dose Plate Preparation (96-well Plate)

Compounds dilutions were prepared in 100% DMSO at 100× final assay concentration.
Compounds were diluted in 100% DMSO to the appropriate maximal concentration.
30 µL compound was added to row A.
21.6 µL of 100% DMSO was added to rows B—H.
Transfer 10 µL from row A into row B (half log dilution).
Transfer 10 µL from row B into row C (half log dilution).
Transfer 10 µL from row C into row D (half log dilution).
Transfer 10 µL from row D into row E (half log dilution).
Transfer 10 µL from row E into row F (half log dilution).
Transfer 10 µL from row F into row G (half log dilution).
Transfer 10 µL from row G into row H (half log dilution).

Working Plate Preparation (96-well Plate)

Compounds were diluted 10-fold in assay buffer.
10 µL compound solution from dose plate was transferred to corresponding well of working plate.
90 µL assay buffer was added to the wells of working plate.
Working solutions contained 10% DMSO in assay buffer (1% DMSO final assay concentration).

Controls
　Total binding (high control) was determined in the absence of unlabelled ligand. A solution of 10% DMSO in assay buffer was prepared.
　Non-specific binding (low control) was determined in the presence of a vast excess (10 µM) of PD 123,319. 1 mM stock solution of PD 123,319 in water was diluted 10-fold with 10% DMSO in assay buffer.

Assay Plate Preparation (96-well Plate)
　15 µL compound solution was transferred to duplicate wells of assay plate. 5 compounds were tested per plate. 15 µL control solutions were transferred to columns 1 and 12 of assay plate.

Procedures for $AT_2$ Receptor Binding Assay
　15 µL of [$^{125}$I]CGP 42112A, at a final concentration of 0.05 nM was added to wells of assay plate.
　Membranes were dispersed using a 21 gauge needle and diluted to the appropriate protein concentration in assay buffer.
　120 µL membrane suspension (15 µg protein/well) was added to wells of assay plate.
　Assay plates were incubated at RT for 2 h.
　Incubations were stopped by rapid filtration through Multiscreen® GF/C plates (Millipore, cat. no. MAFC-NOB50), using Multiscreen®$_{HTS}$ vacuum manifold (Millipore, cat. no. MSVMHTS00) after pre-wetting filters with wash buffer.
　Filters were washed five times with ice-cold wash buffer.
　Filters were dried at RT.
　50 µL MicroScint™ 40 was added to each well.
　Bound $^{125}$I was determined using MicroBeta scintillation counter in Trilux mode, for 1 min per well.

Data Analysis
　Data were fitted with a 4 parameter logistic using Dotmatics Studies to determine $IC_{50}$ values. $K_i$ values were derived using the Cheng-Prussoff equation, using an estimate of [$^{125}$I]CGP 42112A $K_d$ (0.15 nM) determined in a separate saturation binding experiment. Typical assay performance parameters were S/B=11; Z'=0.60. Dissociation constants ($pK_i$) for standard compounds were as follows (mean±S.E.M.): CGP 42112A 9.75±0.06; EMA401 8.71±0.06.
　The results are shown in the following Table:

| Compound | Ki (nM) |
| --- | --- |
| 1 | 7 |
| 2 | 9 |
| 3 | 17 |
| 4 | 15 |
| 5 | 9 |
| 6 | 26 |
| 7 | 50 |
| 8 | 30 |
| 9 | 23 |
| 10 | 21 |

REFERENCES

Chakrabarty et al., 2008, Estrogen elicits dorsal root ganglion axon sprouting via a rennin-angiotensin system. *Endocrinology*, 149(7):3452-3460.
Clere et al., 2010, Deficiency or blockade of angiotensin II type 2 receptor delays tumorigenesis by inhibiting malignant cell proliferation and angiogenesis. *Int. J. Cancer*, 127: 2279-2291.
Izu et al., 2009, Angiotensin II Type 2 receptor blockade increases bone mass. *J. Biol. Chem.*, 284(8):4857-4864.
Reger et al., 2010, Heterocycle-substituted proline dipeptides as potent VLA-4 antagonists. *Biorg. & Med. Chem. Lett.*, 20:1173-1176.
Steckelings et al., 2005, The $AT_2$ receptor—A matter of love and hate. *Peptides*, 26:1401-1409.
Wallinder et al., 2008, Selective angiotensin II $AT_2$ receptor agonists: Benzamide structure-activity relationships. *Bioorganic & Medicinal Chemistry*, 16:6841-6849.
Wan et al., 2004, Design, Synthesis and biological evaluation of the first selective nonpeptide $AT_2$ receptor agonist. *J. Med. Chem.*, 47:5995-6008.
Wexler et al., 1996, Nonpeptide angiotensin II receptor antagonists: The next generation in antihypertensive therapy. *J. Med. Chem.*, 39(3):325-656.

The claims defining the invention are as follows:
1. A compound of formula (I):

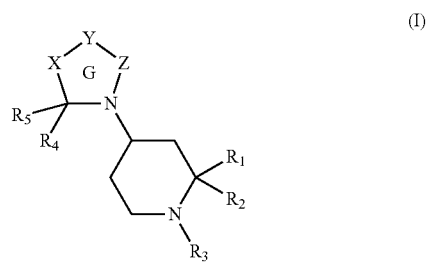

wherein Ring G is a 5 to 8 membered ring and
X is absent or is selected from —(CR$_6$R$_7$)$_n$—, —W—, —(CR$_6$R$_7$)$_m$—W—, —W—(CR$_6$R$_7$)m— and —(CR$_6$R$_7$)$_p$—W—(CR$_6$R$_7$)$_p$—;
Y is —CR$_8$CR$_9$— wherein R$_8$ and R$_9$ together with the carbon atoms to which they are attached form an optionally substituted aromatic or heteroaromatic ring or ring system;
Z is absent or is selected from —CR$_4$R$_5$—, —CR$_6$R$_7$CR$_4$R$_5$—, —W—CR$_4$R$_5$—;
W is selected from —O—, —S—, —S(O)—, —S(O)$_2$—, —C(O)—, —NR$_{10}$—, —C(O)N(R$_{11}$)—, —N(R$_{11}$)C (O)—, —C(O)O—, —OC(O)—, —S(O)$_2$N(R$_{11}$)—, —N(R$_{11}$)S(O)$_2$—, —N(R$_{11}$)C(O)N(R$_{11}$)— and —N(R$_{11}$)S(O)$_2$N(R$_{11}$)—;
R$_1$ is selected from —CO$_2$H, —CH$_2$CO$_2$H, —C(O)C(O) OH, —CH$_2$OH, —C(O)NH$_2$, —CN, —CH$_2$C(O)NH$_2$, —CH$_2$CN, a carboxylic acid bioisostere and —CH$_2$carboxylic acid bioisostere;
R$_2$ is selected from hydrogen, alkyl, alkenyl, alkynyl, —C$_{1-6}$alkyleneR$_{12}$, —C$_{2-6}$alkenyleneR$_{12}$ and —C$_{2-6}$alkynyleneR$_{12}$;
R$_3$ is selected from —C(O)CH(aryl)(aryl) and —C(O)N (aryl)(aryl);
Each R$_4$ and R$_5$ are independently selected from hydrogen, alkyl, alkenyl, alkynyl, —OC(R$_{14}$)$_3$, —CN, —NO$_2$, —N(R$_{13}$)$_2$, —CO$_2$R$_{13}$, —C(O)R$_{13}$, —C(O)N (R$_{13}$)$_2$, —S(O)$_2$R$_{13}$, —S(O)$_2$N(R$_{13}$)$_2$, —C(R$_{14}$)$_3$, cycloalkyl, cycloalkenyl, aryl, heterocyclyl and heteroaryl, or R$_4$ and R$_5$ taken together form a carbonyl group;
R$_6$ and R$_7$ are independently selected from hydrogen, alkyl, alkenyl, alkynyl, —OR$_{13}$, —SR$_{13}$, halo, —CN, —NO$_2$, —N(R$_{13}$)$_2$, —CO$_2$R$_{13}$, —C(O)R$_{13}$, —C(O)N (R$_{13}$)$_2$, —S(O)$_2$R$_{13}$, S(O)$_2$N(R$_{13}$)$_2$, —C(R$_{14}$)$_3$, —OC ($R_{14}$)$_3$, cycloalkyl, cycloalkenyl, aryl, heterocyclyl and heteroaryl, or $R_6$ and $R_7$ taken together form a carbonyl group;

$R_{10}$ is selected from hydrogen, alkyl, alkenyl, alkynyl, cycloalkyl, cycloalkenyl, aryl, heterocyclyl, heteroaryl, —C($R_{14}$)$_3$, —C(O)$R_{13}$, —C(O)N($R_{13}$)$_2$, —S(O)$R_{13}$, —S(O)$_2R_{13}$, —S(O)$_2$N($R_{13}$)$_2$ and —CO$_2R_{13}$;

$R_{11}$ is selected from hydrogen and alkyl;

$R_{12}$ is selected from cycloalkyl, cycloalkenyl, aryl, heterocyclyl and heteroaryl;

Each $R_{13}$ is independently selected from hydrogen, alkyl, alkenyl, alkynyl, cycloalkyl, cycloalkenyl, aryl, heterocyclyl and heteroaryl;

Each $R_{14}$ is independently selected from hydrogen and halo;

n is selected from an integer from 1 to 4;

m is selected from an integer from 1 to 3;

p is selected from an integer of 1 or 2;

wherein each alkyl, alkenyl, alkynyl, cycloalkyl, cycloalkenyl, aryl, heterocyclyl and heteroaryl may be optionally substituted; or a pharmaceutically acceptable salt thereof.

2. A compound of formula (I), according to claim 1, wherein Ring G is a 5 to 8 membered ring and
X is —(CR$_6$R$_7$)$_n$— or —(CR$_6$R$_7$)$_m$—W—;
Y is —CR$_8$CR$_9$— wherein R$_8$ and R$_9$ together with the carbon atoms to which they are attached form an optionally substituted phenyl;
Z is absent;
W is —O— or —S(O)$_2$—;
R$_1$ is —CO$_2$H or a carboxylic acid bioisostere;
R$_2$ is hydrogen;
R$_3$ is —C(O)CH(aryl)(aryl);
R$_4$ and R$_5$ are hydrogen;
R$_6$ and R$_7$ are hydrogen;
n is selected from an integer from 1 to 4;
m is selected from an integer from 1 to 3;
or
a pharmaceutically acceptable salt thereof.

3. A compound according to claim 1, wherein R$_1$ is —CO$_2$H or 13 C(O)NHSO$_2$C$_{3-8}$cycloalkyl, or
a pharmaceutically acceptable salt thereof.

4. A compound according to claim 1, wherein R$_3$ is —C(O)CH(phenyl)(phenyl), or
a pharmaceutically acceptable salt thereof.

5. A compound according to claim 1, wherein n is 1, 2 or 4, or
a pharmaceutically acceptable salt thereof.

6. A compound according to claim 1, wherein m is 1 or 2, or
a pharmaceutically acceptable salt thereof.

7. A compound according to claim 1 which is a compound of formula (II):

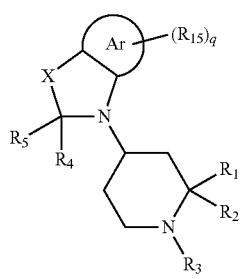

(II)

wherein
X is selected from —(CR$_6$R$_7$)$_n$—, —W—, —(CR$_6$R$_7$)$_m$—W—, —W—(CR$_6$R$_7$)m— and —(CR$_6$R$_7$)$_p$—W—(CR$_6$R$_7$)$_p$—;

Ar is an aromatic or heteroaromatic ring or ring system;

R$_1$ is selected from —CO$_2$H, —CH$_2$CO$_2$H, —C(O)C(O)OH, —CH$_2$OH, —C(O)NH$_2$, —CN, —CH$_2$C(O)NH$_2$, —CH$_2$CN, a carboxylic acid bioisostere and —CH$_2$carboxylic acid bioisostere;

R$_2$ is selected from hydrogen, alkyl, alkenyl, alkynyl, —C$_{1-6}$alkyleneR$_{12}$, —C$_{2-6}$alkenyleneR$_{12}$ and —C$_{2-6}$alkynyleneR$_{12}$;

R$_3$ is selected from —C(O)CH(aryl)(aryl) and —C(O)N(aryl)(aryl);

Each R$_4$ and R$_5$ are independently selected from hydrogen, alkyl, alkenyl, alkynyl, —OC(R$_{14}$)$_3$, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, —S(O)$_2$N(R$_{13}$)$_2$, —C(R$_{14}$)$_3$, cycloalkyl, cycloalkenyl, aryl, heterocyclyl and heteroaryl, or R$_4$ and R$_5$ taken together form a carbonyl group;

R$_6$ and R$_7$ are independently selected from hydrogen, alkyl, alkenyl, alkynyl, —OR$_{13}$, —SR$_{13}$, halo, —CN, —NO$_2$, —N(R$_{13}$)$_2$, —CO$_2$R$_{13}$, —C(O)R$_{13}$, —C(O)N(R$_{13}$)$_2$, —S(O)$_2$R$_{13}$, S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl, or R$_6$ and R$_7$ taken together form a carbonyl group;

W is selected from —O—, —S—, —S(O)—, —S(O)$_2$—, —C(O)—, —NR$_{10}$—, —C(O)N(R$_{11}$)—, —N(R$_{11}$)C(O)—, —C(O)O—, —OC(O)—, —S(O)$_2$N(R$_{11}$)—, —N(R$_{11}$)S(O)$_2$—, —N(R$_{11}$)C(O)N(R$_{11}$)— and —N(R$_{11}$)S(O)$_2$N(R$_{11}$)—;

R$_{10}$ is selected from hydrogen, alkyl, alkenyl, alkynyl, cycloalkyl, cycloalkenyl, aryl, heterocyclyl, heteroaryl, —C(R$_{14}$)$_3$, —C(O)R$_{13}$, —C(O)N(R$_{13}$)$_2$, —S(O)R$_{13}$, —S(O)$_2$R$_{13}$, —S(O)$_2$N(R$_{13}$)$_2$ and —CO$_2$R$_{13}$;

R$_{11}$ is selected from hydrogen and alkyl;

R$_{12}$ is selected from cycloalkyl, cycloalkenyl, aryl, heterocyclyl and heteroaryl;

Each R$_{13}$ is independently selected from hydrogen, alkyl, alkenyl, alkynyl, cycloalkyl, cycloalkenyl, aryl, heterocyclyl and heteroaryl;

Each R$_{14}$ is independently selected from hydrogen and halo;

Each R$_{15}$ is independently selected from —C$_{1-6}$alkyl, —C$_{2-6}$alkenyl, —C$_{2-6}$alkynyl, —OR$_{13}$, —SR$_{13}$, halo, —CN, —NO$_2$, —N(R$_{13}$)$_2$, —CO$_2$R$_{13}$, —CON(R$_{13}$)$_2$, —C(O)R$_{13}$, —S(O)$_2$R$_{13}$, —S(O)$_2$N(R$_{13}$)$_2$, —C(R$_{14}$)$_3$, —OC(R$_{14}$)$_3$, cycloalkyl, cycloalkenyl, aryl, heterocyclyl and heteroaryl;

m is selected from an integer from 1 to 3;
n is selected from an integer from 1 to 4;
p is selected from an integer of 1 or 2; and
q is 0 or an integer of 1 to 4;

wherein each alkyl, alkenyl, alkynyl, cycloalkyl, cycloalkenyl, aryl, heterocyclyl and heteroaryl may be optionally substituted; or a pharmaceutically acceptable salt thereof.

8. A compound of formula (II), according to claim 7, wherein
X is —(CR$_6$R$_7$)$_n$— or —(CR$_6$R$_7$)$_m$—W—;
Ar is an aromatic ring system;
R$_1$ is —CO$_2$H or a carboxylic acid bioisostere;
R$_2$ is hydrogen;
R$_3$ is —C(O)CH(aryl)(aryl);
R$_4$ and R$_5$ are hydrogen;

$R_6$ and $R_7$ are hydrogen;
W is —O— or —S(O)$_2$—;
$R_{13}$ is alkyl;
Each $R_{15}$ is independently selected from —$C_{1-6}$alkyl, —$OR_{13}$, halo and —CN;
m is selected from an integer from 1 to 3;
n is selected from an integer from 1 to 4;
q is 0 or an integer of 1 to 4;
or
a pharmaceutically acceptable salt thereof.

9. A compound according to claim 7, wherein
$R_1$ is —CO$_2$H or —C(O)NHSO$_2$C$_{3-8}$cycloalkyl;
$R_3$ is —C(O)CH(phenyl)(phenyl); and
Ar is phenyl; or
a pharmaceutically acceptable salt thereof.

10. A compound according to claim 7, wherein
n is 1, 2 or 4;
m is 1 or 2; and
q is 1 or 2; or
a pharmaceutically acceptable salt thereof.

11. A pharmaceutical composition comprising an effective amount of the compound of formula (I) according to claim 1 or a pharmaceutically acceptable salt thereof and a pharmaceutically acceptable carrier.

12. A compound accordingly to claim 1, wherein the compound is selected from the group consisting of:
 (2S,4R)-4-(7,8-Difluoro-3,4-dihydrobenzo[b][1,4]oxazepin-5(2H)-yl)-1-(2,2-diphenylacetyl)piperidine-2-carboxylic acid;
 (2S,4R)-1-(2,2-Diphenylacetyl)-4-(8-fluoro-3,4 dihydrobenzo[b][1,4]oxazepin-5(2H) -yl)piperidine-2-carboxylic acid;
 (2S,4R)-1-(2,2-Diphenylacetyl)-4-(7-fluoro-3,4dihydrobenzo[b][1,4]oxazepin-5(2H) -yl)piperidine-2-carboxylic acid;
 (2S,4R)-4-(3,4-Dihydrobenzo[b][1,4]oxazepin-5(2H)-yl)-1-(2,2-diphenylacetyl)piperidine-2-carboxylic acid; and
 (2S,4R)-1-(2,2-diphenylacetyl)-4-(7-methoxy-2,3,4,5-tetrahydro-1H-benzo[b]azepin-1-yl)piperidine-2-carboxylic acid,
or a pharmaceutically acceptable salt thereof.

13. A pharmaceutical composition comprising an effective amount of a compound of formula (I) according to claim 12, or a pharmaceutically acceptable salt thereof, and a pharmaceutically acceptable carrier.

14. A compound accordingly to claim 1, wherein the compound is selected from the group consisting of:
 (2S,4R)-1-(2,2-diphenylacetyl)-4-(2,3,4,5 -tetrahydro-1H-benzo[b] azepin-1-yl)piperidine -2carboxylic acid;
 (2S,4R)-4-(7,8-difluoro-2,3 ,4, 5-tetrahydro-1H-benzo[b] azepin-1-yl)-1-(2,2-diphenylacetyl)piperidine-2-carboxylic acid;
 (2S,4R)-1-(2,2-diphenylacetyl)-4-(7-fluoro-2,3 ,4,5 -tetrahydro-1H-benz[b]azepin-1-yl)piperidine-2-carboxylic acid;
 (2S,4R)-1-(2,2-diphenylacetyl)-4-(8-fluoro-2,3 ,4,5 -tetrahydro-1H-benzo[b]azepin-1-yl)piperidine-2-carboxylic acid; and
 (2S,4S)-1-(2,2-diphenylacetyl)-4-(8-fluoro-2,3 ,4,5 -tetrahydro-1H-benzo[b]azepin-1-yl)piperidine-2-carboxylic acid,
or a pharmaceutically acceptable salt thereof.

15. A pharmaceutical composition comprising an effective amount of a compound of formula (I) according to claim 14, or a pharmaceutically acceptable salt thereof, and a pharmaceutically acceptable carrier.

* * * * *